(12) United States Patent
Thisted et al.

(10) Patent No.: US 7,713,723 B1
(45) Date of Patent: May 11, 2010

(54) ALPHA-AMYLASE MUTANTS WITH ALTERED PROPERTIES

(75) Inventors: Thomas Thisted, Rungsted Kyst (DK); Soren Kjaerulff, Vanlose (DK); Carsten Andersen, Vaerlose (DK); Claus Crone Fuglsang, Niva (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/645,116

(22) Filed: Dec. 22, 2009

Related U.S. Application Data

(63) Continuation of application No. 12/566,238, filed on Sep. 24, 2009, now abandoned, which is a continuation of application No. 10/630,203, filed on Jul. 29, 2003, now abandoned, which is a continuation of application No. 09/918,543, filed on Jul. 31, 2001, now abandoned.

(60) Provisional application No. 60/225,140, filed on Aug. 14, 2000, provisional application No. 60/233,986, filed on Sep. 20, 2000, provisional application No. 60/249,104, filed on Nov. 16, 2000, provisional application No. 60/286,869, filed on Apr. 26, 2001.

(30) Foreign Application Priority Data

| Aug. 1, 2000 | (DK) | ................................ 2000 01160 |
| Sep. 12, 2000 | (DK) | ................................ 2000 01354 |
| Nov. 10, 2000 | (DK) | ................................ 2000 01687 |
| Apr. 26, 2001 | (DK) | ................................ 2001 00655 |

(51) Int. Cl.
C12N 9/28 (2006.01)

(52) U.S. Cl. ..................................... 435/202; 536/23.2
(58) Field of Classification Search ........................ None
See application file for complete search history.

(56) References Cited

U.S. PATENT DOCUMENTS

| 4,769,327 | A | 9/1988 | Stephens et al. |
|---|---|---|---|
| 5,093,257 | A | 3/1992 | Gray |
| 5,234,823 | A | 8/1993 | Diderichsen et al. |
| 5,364,782 | A | 11/1994 | Quax et al. |
| 5,736,499 | A | 4/1998 | Mitchinson et al. |
| 5,763,385 | A | 6/1998 | Bott et al. |
| 5,801,043 | A | 9/1998 | Bisgard-Frantzen et al. |
| 5,824,532 | A | 10/1998 | Barnett et al. |
| 5,830,837 | A | 11/1998 | Bisgard-Frantzen et al. |
| 5,849,549 | A | 12/1998 | Barnett et al. |
| 5,856,164 | A | 1/1999 | Outtrup et al. |
| 5,928,381 | A | 7/1999 | Toft et al. |
| 5,958,739 | A | 9/1999 | Mitchinson et al. |
| 5,989,169 | A | 11/1999 | Svendsen et al. |
| 6,008,026 | A | 12/1999 | Day |
| 6,015,783 | A | 1/2000 | von der Osten et al. |
| 6,017,751 | A | 1/2000 | von der Osten et al. |
| 6,080,568 | A | 6/2000 | Day et al. |
| 6,093,562 | A | * 7/2000 | Bisgård-Frantzen et al. 435/202 |
| 6,187,576 | B1 | 2/2001 | Svendsen et al. |
| 6,197,565 | B1 | 3/2001 | Svendsen et al. |
| 6,204,232 | B1 | 3/2001 | Borchert et al. |
| 6,211,134 | B1 | 4/2001 | Caldwell et al. |
| 6,287,826 | B1 | 9/2001 | Norman et al. |
| 6,297,037 | B1 | 10/2001 | Barnett et al. |
| 6,297,038 | B1 | 10/2001 | Bisgard-Frantzen et al. |
| 6,361,989 | B1 | 3/2002 | Svendsen et al. |
| 6,403,355 | B1 | 6/2002 | Hagihara et al. |
| 6,410,295 | B1 | 6/2002 | Andersen et al. |
| 6,486,113 | B1 | 11/2002 | Hatada et al. |
| 6,623,948 | B1 | 9/2003 | Outtrup et al. |
| 6,673,589 | B2 | 1/2004 | Borchert et al. |
| 6,867,031 | B2 | 3/2005 | Bisgard-Frantzen et al. |
| 6,887,986 | B1 | 5/2005 | Svendsen et al. |
| 6,939,703 | B2 | 9/2005 | Van Der Laan et al. |
| 7,306,936 | B2 | 12/2007 | Andersen et al. |
| 7,378,264 | B2 | 5/2008 | Svendsen et al. |
| 7,432,099 | B2 | 10/2008 | Andersen et al. |
| 7,541,026 | B2 | 6/2009 | Power et al. |
| 7,601,527 | B2 | 10/2009 | Svendsen et al. |
| 7,625,737 | B2 | 12/2009 | Svendsen et al. |
| 2001/0039253 | A1 | 11/2001 | Borchert et al. |
| 2002/0068352 | A1 | 6/2002 | Svendsen et al. |
| 2003/0129718 | A1 | 7/2003 | Andersen et al. |
| 2005/0250663 | A1 | 11/2005 | Thisted et al. |
| 2008/0274938 | A1 | 11/2008 | Poulose et al. |
| 2009/0203109 | A1 | 8/2009 | Svendsen et al. |

FOREIGN PATENT DOCUMENTS

| EP | 0 252 666 | 1/1988 |
|---|---|---|
| EP | 0 273 268 | 7/1988 |
| EP | 0 285 123 | 10/1988 |
| EP | 0 352 073 | 1/1990 |
| EP | 1 022 334 | 7/2000 |
| FR | 2665178 | 1/1992 |
| FR | 2676456 | 11/1992 |
| IN | 184770 | 9/1995 |
| JP | 62-104580 | 5/1987 |
| JP | 8-289788 | 11/1996 |
| NZ | 524303 | 12/2009 |

(Continued)

OTHER PUBLICATIONS

Takkinen et al., SwissProt Database Accession No. P00692 (1986).

(Continued)

*Primary Examiner*—Rebecca Prouty
(74) *Attorney, Agent, or Firm*—Elias Lambiris

(57) ABSTRACT

The present invention relates to variants (mutants) of parent Termamyl-like alpha-amylases, which variant has alpha-amylase activity and exhibits altered stability, in particular at high temperatures and/or at low pH relative, and/or low $Ca^{2+}$ to the parent alpha-amylase.

17 Claims, 3 Drawing Sheets

FOREIGN PATENT DOCUMENTS

| | | |
|---|---|---|
| WO | WO 87/00202 | 1/1987 |
| WO | WO 91/00353 | 1/1991 |
| WO | WO 94/02597 | 2/1994 |
| WO | WO 94/18314 | 8/1994 |
| WO | WO 95/26397 | 10/1995 |
| WO | WO 96/05295 | 2/1996 |
| WO | WO 96/23874 | 8/1996 |
| WO | WO 96/30481 | 10/1996 |
| WO | WO 97/00324 | 1/1997 |
| WO | WO 97/32961 | 9/1997 |
| WO | WO 97/41213 | 11/1997 |
| WO | WO 97/43424 | 11/1997 |
| WO | WO 98/05748 | 2/1998 |
| WO | WO 98/16633 | 4/1998 |
| WO | WO 98/26078 | 6/1998 |
| WO | WO 99/19467 | 4/1999 |
| WO | WO 99/20723 | 4/1999 |
| WO | WO 99/23211 | 5/1999 |
| WO | WO 99/09183 | 2/2000 |
| WO | WO 00/29560 | 5/2000 |
| WO | WO 00/60058 | 10/2000 |
| WO | WO 00/60059 | 10/2000 |
| WO | WO 00/75344 | 12/2000 |
| WO | WO 01/47956 | 7/2001 |
| WO | WO 01/64852 | 9/2001 |
| WO | WO 01/96537 | 12/2001 |
| WO | 02/31124 * | 4/2002 |

OTHER PUBLICATIONS

Tsukamoto et al., SwissProt Database Accession No. P195712 (1991).

Conrad et al, European Journal of Biochemistry, vol. 230, pp. 481-490 (1995).

Edwards et al., GenBank Database, Accession No. AAA54800, Sequence 14 from WO 87/00202 (1987).

Edwards et al., GenBank Database, Accession No. AAA54806, Sequence 22 from WO 87/00202 (1987).

Gray et al, Journal of Bacteriology, vol. 166, No. 2, pp. 635-643 (1986).

Ihara et al, Journal of Biochemistry, vol. 98, No. 1, pp. 95-103 (1985).

Jorgensen et al, FEMS Microbiology Letters, vol. 77, pp. 271-276 (1991).

Muscholl-Silberhorn, Journal of Bacteriology, vol. 182, No. 13, pp. 3816-3825 (2000).

Muscholl-Silberhorn, Molecular Microbiology, vol. 34, No. 3, pp. 620-630 (1999).

Nakajima et al, Journal of Bacteriology, vol. 163, No. 1, pp. 401-406 (1985).

Sloma et al., GenBank Database, Accession No. AAA55247, Sequence 3 From EP 0352073 (1990).

Stephens et al., GenBank Database, Accession No. AAA01437, Sequence 1 from U.S. Appl. No. 4,769,327 (1988).

Vihinen et al., Protein Engineering, vol. 7, No. 10, pp. 1255-1259 (1994).

Xu et al, Gongye Weishengwu, vol. 23, No. 2, pp. 1-7 (1993).

Yuuki et al, Journal of Biochemistry, vol. 98, No. 5, pp. 1147-1156 (1985).

Suzuki et al., The Journal of Biological Chemistry, vol. 264, No. 32, pp. 18933-18938 (1989).

Tomazic et al., The Journal of Biological Chemistry, vol. 263, No. 7, pp. 3092-3096 (1988).

* cited by examiner

```
        1                                                                    50
1    HHNGTNGTMM  QYFEWHLPND  GNHWNRLRDD  ASNLRNRGIT  AIWIPPAWKG
2    HHNGTNGTMM  QYFEWYLPND  GNHWNRLRDD  AANLKSKGIT  AVWIPPAWKG
3    ....VNGTLM  QYFEWYTPND  GQHWKRLQND  AEHLSDIGIT  AVWIPPAYKG
4    ..ANLNGTLM  QYFEWYMPND  GQHWRRLQND  SAYLAEHGIT  AVWIPPAYKG
5    .AAPFNGTMM  QYFEWYLPDD  GTLWTKVANE  ANNLSSLGIT  ALWLPPAYKG 51                                                                  100
1    TSQNDVGYGA  YDLYDLGEFN  QKGTVRTKYG  TRSQLESAIH  ALKNNGVQVY
2    TSQNDVGYGA  YDLYDLGEFN  QKGTVRTKYG  TRNQLQAAVT  SLKNNGIQVY
3    LSQSDNGYGP  YDLYDLGEFQ  QKGTVRTKYG  TKSELQDAIG  SLHSRNVQVY
4    TSQADVGYGA  YDLYDLGEFH  QKGTVRTKYG  TKGELQSAIK  SLHSRDINVY
5    TSRSDVGYGV  YDLYDLGEFN  QKGTVRTKYG  TKAQYLQAIQ  AAHAAGMQVY 101                                                                 150
1    GDVVMNHKGG  ADATENVLAV  EVNPNNRNQE  ISGDYTIEAW  TKFDFPGRGN
2    GDVVMNHKGG  ADGTEIVNAV  EVNRSNRNQE  TSGEYAIEAW  TKFDFPGRGN
3    GDVVLNHKAG  ADATEDVTAV  EVNPANRNQE  TSEEYQIKAW  TDFRFPGRGN
4    GDVVINHKGG  ADATEDVTAV  EVDPADRNRV  ISGEHLIKAW  THFHFPGRGS
5    ADVVFDHKGG  ADGTEWVDAV  EVNPSDRNQE  ISGTYQIQAW  TKFDFPGRGN 151                                                                 200
1    TYSDFKWRWY  HFDGVDWDQS  RQFQNRIYKF  RGDGKAWDWE  VDSENGNYDY
2    NHSSFKWRWY  HFDGTDWDQS  RQLQNKIYKF  RGTGKAWDWE  VDTENGNYDY
3    TYSDFKWHWY  HFDGADWDES  RKI.SRIFKF  RGEGKAWDWE  VSSENGNYDY
4    TYSDFKWHWY  HFDGTDWDES  RKL.NRIYKF  ..QGKAWDWE  VSNENGNYDY
5    TYSSFKWRWY  HFDGVDWDES  RKL.SRIYKF  RGIGKAWDWE  VDTENGNYDY
```

Figure 1A

```
      201                                                       250
1     LMYADVDMDH PEVVNELRRW GEWYTNTLNL DGFRIDAVKH IKYSFTRDWL
2     LMYADVDMDH PEVIHELRNW GVWYTNTLNL DGFRIDAVKH IKYSFTRDWL
3     LMYADVDYDH PDVVAETKKW GIWYANELSL DGFRIDAAKH IKFSFLRDWV
4     LMYADIDYDH PDVAAEIKRW GTWYANELQL DGFRLDAVKH IKFSFLRDWV
5     LMYADLDMDH PEVVTELKNW GKWYVNTTNI DGFRLDAVKH IKFSFFPDWL 251                                                       300
1     THVRNATGKE MFAVAEFWKN DLGALENYLN KTNWNHSVFD VPLHYNLYNA
2     THVRNTTGKP MFAVAEFWKN DLGAIENYLN KTSWNHSAFD VPLHYNLYNA
3     QAVRQATGKE MFTVAEYWQN NAGKLENYLN KTSFNQSVFD VPLHFNLQAA
4     NHVREKTGKE MFTVAEYWQN DLGALENYLN KTNFNHSVFD VPLHYQFHAA
5     SYVRSQTGKP LFTVGEYWSY DINKLHNYIT KTDGTMSLFD APLHNKFYTA 301                                                       350
1     SNSGGNYDMA KLLNGTVVQK HPMHAVTFVD NHDSQPGESL ESFVQEWFKP
2     SNSGGYYDMR NILNGSVVQK HPTHAVTFVD NHDSQPGEAL ESFVQQWFKP
3     SSQGGGYDMR RLLDGTVVSR HPEKAVTFVE NHDTQPGQSL ESTVQTWFKP
4     STQGGGYDMR KLLNGTVVSK HPLKSVTFVD NHDTQPGQSL ESTVQTWFKP
5     SKSGGAFDMR TLMTNTLMKD QPTLAVTFVD NHDTEPGQAL QSWVDPWFKP 351                                                       400
1     LAYALILTRE QGYPSVFYGD YYGIPTHS.. .VPAMKAKID PILEARQNFA
2     LAYALVLTRE QGYPSVFYGD YYGIPTHG.. .VPAMKSKID PLLQARQTFA
3     LAYAFILTRE SGYPQVFYGD MYGTKGTSPK EIPSLKDNIE PILKARKEYA
4     LAYAFILTRE SGYPQVFYGD MYGTKGDSQR EIPALKHKIE PILKARKQYA
5     LAYAFILTRQ EGYPCVFYGD YYGIPQYN.. .IPSLKSKID PLLIARRDYA 401                                                       450
1     YGTQHDYFDH HNIIGWTREG NTTHPNSGLA TIMSDGPGGE KWMYVGQNKA
2     YGTQHDYFDH HDIIGWTREG NSSHPNSGLA TIMSDGPGGN KWMYVGKNKA
3     YGPQHDYIDH PDVIGWTREG DSSAAKSGLA ALITDGPGGS KRMYAGLKNA
4     YGAQHDYFDH HDIVGWTREG DSSVANSGLA ALITDGPGGA KRMYVGRQNA
5     YGTQHDYLDH SDIIGWTREG GTEKPGSGLA ALITDGPGGS KWMYVGKQHA
```

Figure 1B

```
      451                                                      500
1     GQVWHDITGN KPGTVTINAD GWANFSVNGG SVSIWVKR.. ..........
2     GQVWRDITGN RTGTVTINAD GWGNFSVNGG SVSVWVKQ.. ..........
3     GETWYDITGN RSDTVKIGSD GWGEFHVNDG SVSIYVQ... ..........
4     GETWHDITGN RSEPVVINSE GWGEFHVNGG SVSIYVQR.. ..........
5     GKVFYDLTGN RSDTVTINSD GWGEFKVNGG SVSVWVPRKT TVSTIARPIT 501        519
1     .......... .........
2     .......... .........
3     .......... .........
4     .......... .........
5     TRPWTGEFVR WTEPRLVAW
```

Figure 1C

SEQUENCE LISTING

<160> NUMBER OF SEQ ID NOS: 30

<210> SEQ ID NO 1
<211> LENGTH: 1455
<212> TYPE: DNA
<213> ORGANISM: Bacillus species
<220> FEATURE:
<221> NAME/KEY: CDS
<222> LOCATION: (1)..(1455)

<400> SEQUENCE: 1

| | | | | | | | | | | | | | | | | |
|---|---|---|---|---|---|---|---|---|---|---|---|---|---|---|---|---|
| cat | cat | aat | gga | aca | aat | ggt | act | atg | atg | caa | tat | ttc | gaa | tgg | tat | 48 |
| His | His | Asn | Gly | Thr | Asn | Gly | Thr | Met | Met | Gln | Tyr | Phe | Glu | Trp | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | cca | aat | gac | ggg | aat | cat | tgg | aac | agg | ttg | agg | gat | gac | gca | gct | 96 |
| Leu | Pro | Asn | Asp | Gly | Asn | His | Trp | Asn | Arg | Leu | Arg | Asp | Asp | Ala | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | tta | aag | agt | aaa | ggg | ata | aca | gct | gta | tgg | atc | cca | cct | gca | tgg | 144 |
| Asn | Leu | Lys | Ser | Lys | Gly | Ile | Thr | Ala | Val | Trp | Ile | Pro | Pro | Ala | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | ggg | act | tcc | cag | aat | gat | gta | ggt | tat | gga | gcc | tat | gat | tta | tat | 192 |
| Lys | Gly | Thr | Ser | Gln | Asn | Asp | Val | Gly | Tyr | Gly | Ala | Tyr | Asp | Leu | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| gat | ctt | gga | gag | ttt | aac | cag | aag | ggg | acg | gtt | cgt | aca | aaa | tat | gga | 240 |
| Asp | Leu | Gly | Glu | Phe | Asn | Gln | Lys | Gly | Thr | Val | Arg | Thr | Lys | Tyr | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | cgc | aac | cag | cta | cag | gct | gcg | gtg | acc | tct | tta | aaa | aat | aac | ggc | 288 |
| Thr | Arg | Asn | Gln | Leu | Gln | Ala | Ala | Val | Thr | Ser | Leu | Lys | Asn | Asn | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| att | cag | gta | tat | ggt | gat | gtc | gtc | atg | aat | cat | aaa | ggt | gga | gca | gat | 336 |
| Ile | Gln | Val | Tyr | Gly | Asp | Val | Val | Met | Asn | His | Lys | Gly | Gly | Ala | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ggt | acg | gaa | att | gta | aat | gcg | gta | gaa | gtg | aat | cgg | agc | aac | cga | aac | 384 |
| Gly | Thr | Glu | Ile | Val | Asn | Ala | Val | Glu | Val | Asn | Arg | Ser | Asn | Arg | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | gaa | acc | tca | gga | gag | tat | gca | ata | gaa | gcg | tgg | aca | aag | ttt | gat | 432 |
| Gln | Glu | Thr | Ser | Gly | Glu | Tyr | Ala | Ile | Glu | Ala | Trp | Thr | Lys | Phe | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| ttt | cct | gga | aga | gga | aat | aac | cat | tcc | agc | ttt | aag | tgg | cgc | tgg | tat | 480 |
| Phe | Pro | Gly | Arg | Gly | Asn | Asn | His | Ser | Ser | Phe | Lys | Trp | Arg | Trp | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cat | ttt | gat | ggg | aca | gat | tgg | gat | cag | tca | cgc | cag | ctt | caa | aac | aaa | 528 |
| His | Phe | Asp | Gly | Thr | Asp | Trp | Asp | Gln | Ser | Arg | Gln | Leu | Gln | Asn | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| ata | tat | aaa | ttc | agg | gga | aca | ggc | aag | gcc | tgg | gac | tgg | gaa | gtc | gat | 576 |
| Ile | Tyr | Lys | Phe | Arg | Gly | Thr | Gly | Lys | Ala | Trp | Asp | Trp | Glu | Val | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| aca | gag | aat | ggc | aac | tat | gac | tat | ctt | atg | tat | gca | gac | gtg | gat | atg | 624 |
| Thr | Glu | Asn | Gly | Asn | Tyr | Asp | Tyr | Leu | Met | Tyr | Ala | Asp | Val | Asp | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| gat | cac | cca | gaa | gta | ata | cat | gaa | ctt | aga | aac | tgg | gga | gtg | tgg | tat | 672 |
| Asp | His | Pro | Glu | Val | Ile | His | Glu | Leu | Arg | Asn | Trp | Gly | Val | Trp | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| acg | aat | aca | ctg | aac | ctt | gat | gga | ttt | aga | ata | gat | gca | gtg | aaa | cat | 720 |
| Thr | Asn | Thr | Leu | Asn | Leu | Asp | Gly | Phe | Arg | Ile | Asp | Ala | Val | Lys | His | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ata | aaa | tat | agc | ttt | acg | aga | gat | tgg | ctt | aca | cat | gtg | cgt | aac | acc | 768 |
| Ile | Lys | Tyr | Ser | Phe | Thr | Arg | Asp | Trp | Leu | Thr | His | Val | Arg | Asn | Thr | |
| | | | | 245 | | | | | 250 | | | | | 255 | | |

```
aca ggt aaa cca atg ttt gca gtg gct gag ttt tgg aaa aat gac ctt      816
Thr Gly Lys Pro Met Phe Ala Val Ala Glu Phe Trp Lys Asn Asp Leu
        260                 265                 270 ggt gca att gaa aac tat ttg aat aaa aca agt tgg aat cac tcg gtg      864
Gly Ala Ile Glu Asn Tyr Leu Asn Lys Thr Ser Trp Asn His Ser Val
    275                 280                 285 ttt gat gtt cct ctc cac tat aat ttg tac aat gca tct aat agc ggt      912
Phe Asp Val Pro Leu His Tyr Asn Leu Tyr Asn Ala Ser Asn Ser Gly
290                 295                 300 ggt tat tat gat atg aga aat att tta aat ggt tct gtg gtg caa aaa      960
Gly Tyr Tyr Asp Met Arg Asn Ile Leu Asn Gly Ser Val Val Gln Lys
305                 310                 315                 320 cat cca aca cat gcc gtt act ttt gtt gat aac cat gat tct cag ccc     1008
His Pro Thr His Ala Val Thr Phe Val Asp Asn His Asp Ser Gln Pro
            325                 330                 335 ggg gaa gca ttg gaa tcc ttt gtt caa caa tgg ttt aaa cca ctt gca     1056
Gly Glu Ala Leu Glu Ser Phe Val Gln Gln Trp Phe Lys Pro Leu Ala
        340                 345                 350 tat gca ttg gtt ctg aca agg gaa caa ggt tat cct tcc gta ttt tat     1104
Tyr Ala Leu Val Leu Thr Arg Glu Gln Gly Tyr Pro Ser Val Phe Tyr
    355                 360                 365 ggg gat tac tac ggt atc cca acc cat ggt gtt ccg gct atg aaa tct     1152
Gly Asp Tyr Tyr Gly Ile Pro Thr His Gly Val Pro Ala Met Lys Ser
370                 375                 380 aaa ata gac cct ctt ctg cag gca cgt caa act ttt gcc tat ggt acg     1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag     1248
Gln His Asp Tyr Phe Asp His His Asp Ile Ile Gly Trp Thr Arg Glu
            405                 410                 415 gga aat agc tcc cat cca aat tca ggc ctt gcc acc att atg tca gat     1296
Gly Asn Ser Ser His Pro Asn Ser Gly Leu Ala Thr Ile Met Ser Asp
        420                 425                 430 ggt cca ggt ggt aac aaa tgg atg tat gtg ggg aaa aat aaa gcg gga     1344
Gly Pro Gly Gly Asn Lys Trp Met Tyr Val Gly Lys Asn Lys Ala Gly
    435                 440                 445 caa gtt tgg aga gat att acc gga aat agg aca ggc acc gtc aca att     1392
Gln Val Trp Arg Asp Ile Thr Gly Asn Arg Thr Gly Thr Val Thr Ile
450                 455                 460 aat gca gac gga tgg ggt aat ttc tct gtt aat gga ggg tcc gtt tcg     1440
Asn Ala Asp Gly Trp Gly Asn Phe Ser Val Asn Gly Gly Ser Val Ser
465                 470                 475                 480 gtt tgg gtg aag caa                                                  1455
Val Trp Val Lys Gln
            485

<210> SEQ ID NO 2
<211> LENGTH: 485
<212> TYPE: PRT
<213> ORGANISM: Bacillus species

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60
```

-continued

```
Asp Leu Gly Glu Phe Asn Gln Lys Gly Thr Val Arg Thr Lys Tyr Gly
 65                  70                  75                  80

Thr Arg Asn Gln Leu Gln Ala Ala Val Thr Ser Leu Lys Asn Asn Gly
             85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480
```

```
Val Trp Val Lys Gln
            485

<210> SEQ ID NO 3
<211> LENGTH: 1455
<212> TYPE: DNA
<213> ORGANISM: Bacillus species
<220> FEATURE:
<221> NAME/KEY: CDS
<222> LOCATION: (1)..(1455)

<400> SEQUENCE: 3 cat cat aat ggg aca aat ggg acg atg atg caa tac ttt gaa tgg cac      48
His His Asn Gly Thr Asn Gly Thr Met Met Gln Tyr Phe Glu Trp His
1               5                   10                  15 ttg cct aat gat ggg aat cac tgg aat aga tta aga gat gat gct agt      96
Leu Pro Asn Asp Gly Asn His Trp Asn Arg Leu Arg Asp Asp Ala Ser
            20                  25                  30 aat cta aga aat aga ggt ata acc gct att tgg att ccg cct gcc tgg     144
Asn Leu Arg Asn Arg Gly Ile Thr Ala Ile Trp Ile Pro Pro Ala Trp
        35                  40                  45 aaa ggg act tcg caa aat gat gtg ggg tat gga gcc tat gat ctt tat     192
Lys Gly Thr Ser Gln Asn Asp Val Gly Tyr Gly Ala Tyr Asp Leu Tyr
    50                  55                  60 gat tta ggg gaa ttt aat caa aag ggg acg gtt cgt act aag tat ggg     240
Asp Leu Gly Glu Phe Asn Gln Lys Gly Thr Val Arg Thr Lys Tyr Gly
65                  70                  75                  80 aca cgt agt caa ttg gag tct gcc atc cat gct tta aag aat aat ggc     288
Thr Arg Ser Gln Leu Glu Ser Ala Ile His Ala Leu Lys Asn Asn Gly
                85                  90                  95 gtt caa gtt tat ggg gat gta gtg atg aac cat aaa gga gga gct gat     336
Val Gln Val Tyr Gly Asp Val Val Met Asn His Lys Gly Gly Ala Asp
            100                 105                 110 gct aca gaa aac gtt ctt gct gtc gag gtg aat cca aat aac cgg aat     384
Ala Thr Glu Asn Val Leu Ala Val Glu Val Asn Pro Asn Asn Arg Asn
        115                 120                 125 caa gaa ata tct ggg gac tac aca att gag gct tgg act aag ttt gat     432
Gln Glu Ile Ser Gly Asp Tyr Thr Ile Glu Ala Trp Thr Lys Phe Asp
    130                 135                 140 ttt cca ggg agg ggt aat aca tac tca gac ttt aaa tgg cgt tgg tat     480
Phe Pro Gly Arg Gly Asn Thr Tyr Ser Asp Phe Lys Trp Arg Trp Tyr
145                 150                 155                 160 cat ttc gat ggt gta gat tgg gat caa tca cga caa ttc caa aat cgt     528
His Phe Asp Gly Val Asp Trp Asp Gln Ser Arg Gln Phe Gln Asn Arg
                165                 170                 175 atc tac aaa ttc cga ggt gat ggt aag gca tgg gat tgg gaa gta gat     576
Ile Tyr Lys Phe Arg Gly Asp Gly Lys Ala Trp Asp Trp Glu Val Asp
            180                 185                 190 tcg gaa aat gga aat tat gat tat tta atg tat gca gat gta gat atg     624
Ser Glu Asn Gly Asn Tyr Asp Tyr Leu Met Tyr Ala Asp Val Asp Met
        195                 200                 205 gat cat ccg gag gta gta aat gag ctt aga aga tgg gga gaa tgg tat     672
Asp His Pro Glu Val Val Asn Glu Leu Arg Arg Trp Gly Glu Trp Tyr
    210                 215                 220 aca aat aca tta aat ctt gat gga ttt agg atc gat gcg gtg aag cat     720
Thr Asn Thr Leu Asn Leu Asp Gly Phe Arg Ile Asp Ala Val Lys His
225                 230                 235                 240 att aaa tat agc ttt aca cgt gat tgg ttg acc cat gta aga aac gca     768
Ile Lys Tyr Ser Phe Thr Arg Asp Trp Leu Thr His Val Arg Asn Ala
                245                 250                 255 acg gga aaa gaa atg ttt gct gtt gct gaa ttt tgg aaa aat gat tta     816
```

```
                    Thr Gly Lys Glu Met Phe Ala Val Ala Glu Phe Trp Lys Asn Asp Leu
                                260                 265                 270 ggt gcc ttg gag aac tat tta aat aaa aca aac tgg aat cat tct gtc              864
Gly Ala Leu Glu Asn Tyr Leu Asn Lys Thr Asn Trp Asn His Ser Val
            275                 280                 285 ttt gat gtc ccc ctt cat tat aat ctt tat aac gcg tca aat agt gga              912
Phe Asp Val Pro Leu His Tyr Asn Leu Tyr Asn Ala Ser Asn Ser Gly
        290                 295                 300 ggc aac tat gac atg gca aaa ctt ctt aat gga acg gtt gtt caa aag              960
Gly Asn Tyr Asp Met Ala Lys Leu Leu Asn Gly Thr Val Val Gln Lys
305                 310                 315                 320 cat cca atg cat gcc gta act ttt gtg gat aat cac gat tct caa cct             1008
His Pro Met His Ala Val Thr Phe Val Asp Asn His Asp Ser Gln Pro
                325                 330                 335 ggg gaa tca tta gaa tca ttt gta caa gaa tgg ttt aag cca ctt gct             1056
Gly Glu Ser Leu Glu Ser Phe Val Gln Glu Trp Phe Lys Pro Leu Ala
            340                 345                 350 tat gcg ctt att tta aca aga gaa caa ggc tat ccc tct gtc ttc tat             1104
Tyr Ala Leu Ile Leu Thr Arg Glu Gln Gly Tyr Pro Ser Val Phe Tyr
        355                 360                 365 ggt gac tac tat gga att cca aca cat agt gtc cca gca atg aaa gcc             1152
Gly Asp Tyr Tyr Gly Ile Pro Thr His Ser Val Pro Ala Met Lys Ala
370                 375                 380 aag att gat cca atc tta gag gcg cgt caa aat ttt gca tat gga aca             1200
Lys Ile Asp Pro Ile Leu Glu Ala Arg Gln Asn Phe Ala Tyr Gly Thr
385                 390                 395                 400 caa cat gat tat ttt gac cat cat aat ata atc gga tgg aca cgt gaa             1248
Gln His Asp Tyr Phe Asp His His Asn Ile Ile Gly Trp Thr Arg Glu
                405                 410                 415 gga aat acc acg cat ccc aat tca gga ctt gcg act atc atg tcg gat             1296
Gly Asn Thr Thr His Pro Asn Ser Gly Leu Ala Thr Ile Met Ser Asp
            420                 425                 430 ggg cca ggg gga gag aaa tgg atg tac gta ggg caa aat aaa gca ggt             1344
Gly Pro Gly Gly Glu Lys Trp Met Tyr Val Gly Gln Asn Lys Ala Gly
        435                 440                 445 caa gtt tgg cat gac ata act gga aat aaa cca gga aca gtt acg atc             1392
Gln Val Trp His Asp Ile Thr Gly Asn Lys Pro Gly Thr Val Thr Ile
450                 455                 460 aat gca gat gga tgg gct aat ttt tca gta aat gga gga tct gtt tcc             1440
Asn Ala Asp Gly Trp Ala Asn Phe Ser Val Asn Gly Gly Ser Val Ser
465                 470                 475                 480 att tgg gtg aaa cga                                                          1455
Ile Trp Val Lys Arg
                485

<210> SEQ ID NO 4
<211> LENGTH: 485
<212> TYPE: PRT
<213> ORGANISM: Bacillus species

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60
```

-continued

```
Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
```

-continued

485

<210> SEQ ID NO 5
<211> LENGTH: 1548
<212> TYPE: DNA
<213> ORGANISM: Bacillus stearothermophilus
<220> FEATURE:
<221> NAME/KEY: CDS
<222> LOCATION: (1)..(1548)

<400> SEQUENCE: 5

| | | | | | | | | | | | | | | | | |
|---|---|---|---|---|---|---|---|---|---|---|---|---|---|---|---|---|
| gcc | gca | ccg | ttt | aac | ggc | acc | atg | atg | cag | tat | ttt | gaa | tgg | tac | ttg | 48 |
| Ala | Ala | Pro | Phe | Asn | Gly | Thr | Met | Met | Gln | Tyr | Phe | Glu | Trp | Tyr | Leu | |
| 1 | | | | 5 | | | | | 10 | | | | | 15 | | |
| ccg | gat | gat | ggc | acg | tta | tgg | acc | aaa | gtg | gcc | aat | gaa | gcc | aac | aac | 96 |
| Pro | Asp | Asp | Gly | Thr | Leu | Trp | Thr | Lys | Val | Ala | Asn | Glu | Ala | Asn | Asn | |
| | | | 20 | | | | | 25 | | | | | 30 | | | |
| tta | tcc | agc | ctt | ggc | atc | acc | gct | ctt | tgg | ctg | ccc | gct | tac | aaa | | 144 |
| Leu | Ser | Ser | Leu | Gly | Ile | Thr | Ala | Leu | Trp | Leu | Pro | Ala | Tyr | Lys | | |
| | 35 | | | | | 40 | | | | | 45 | | | | | |
| gga | aca | agc | cgc | agc | gac | gta | ggg | tac | gga | gta | tac | gac | ttg | tat | gac | 192 |
| Gly | Thr | Ser | Arg | Ser | Asp | Val | Gly | Tyr | Gly | Val | Tyr | Asp | Leu | Tyr | Asp | |
| | 50 | | | | 55 | | | | | 60 | | | | | | |
| ctc | ggc | gaa | ttc | aat | caa | aaa | ggg | acc | gtc | cgc | aca | aaa | tac | gga | aca | 240 |
| Leu | Gly | Glu | Phe | Asn | Gln | Lys | Gly | Thr | Val | Arg | Thr | Lys | Tyr | Gly | Thr | |
| 65 | | | | | 70 | | | | | 75 | | | | | 80 | |
| aaa | gct | caa | tat | ctt | caa | gcc | att | caa | gcc | gcc | cac | gcc | gct | gga | atg | 288 |
| Lys | Ala | Gln | Tyr | Leu | Gln | Ala | Ile | Gln | Ala | Ala | His | Ala | Ala | Gly | Met | |
| | | | | 85 | | | | | 90 | | | | | 95 | | |
| caa | gtg | tac | gcc | gat | gtc | gtg | ttc | gac | cat | aaa | ggc | ggc | gct | gac | ggc | 336 |
| Gln | Val | Tyr | Ala | Asp | Val | Val | Phe | Asp | His | Lys | Gly | Gly | Ala | Asp | Gly | |
| | | | 100 | | | | | 105 | | | | | 110 | | | |
| acg | gaa | tgg | gtg | gac | gcc | gtc | gaa | gtc | aat | ccg | tcc | gac | cgc | aac | caa | 384 |
| Thr | Glu | Trp | Val | Asp | Ala | Val | Glu | Val | Asn | Pro | Ser | Asp | Arg | Asn | Gln | |
| | | 115 | | | | | 120 | | | | | 125 | | | | |
| gaa | atc | tcg | ggc | acc | tat | caa | atc | caa | gca | tgg | acg | aaa | ttt | gat | ttt | 432 |
| Glu | Ile | Ser | Gly | Thr | Tyr | Gln | Ile | Gln | Ala | Trp | Thr | Lys | Phe | Asp | Phe | |
| | 130 | | | | | 135 | | | | | 140 | | | | | |
| ccc | ggg | cgg | ggc | aac | acc | tac | tcc | agc | ttt | aag | tgg | cgc | tgg | tac | cat | 480 |
| Pro | Gly | Arg | Gly | Asn | Thr | Tyr | Ser | Ser | Phe | Lys | Trp | Arg | Trp | Tyr | His | |
| 145 | | | | | 150 | | | | | 155 | | | | | 160 | |
| ttt | gac | ggc | gtt | gat | tgg | gac | gaa | agc | cga | aaa | ttg | agc | cgc | att | tac | 528 |
| Phe | Asp | Gly | Val | Asp | Trp | Asp | Glu | Ser | Arg | Lys | Leu | Ser | Arg | Ile | Tyr | |
| | | | 165 | | | | | 170 | | | | | 175 | | | |
| aaa | ttc | cgc | ggc | atc | ggc | aaa | gcg | tgg | gat | tgg | gaa | gta | gac | acg | gaa | 576 |
| Lys | Phe | Arg | Gly | Ile | Gly | Lys | Ala | Trp | Asp | Trp | Glu | Val | Asp | Thr | Glu | |
| | | 180 | | | | | 185 | | | | | 190 | | | | |
| aac | gga | aac | tat | gac | tac | tta | atg | tat | gcc | gac | ctt | gat | atg | gat | cat | 624 |
| Asn | Gly | Asn | Tyr | Asp | Tyr | Leu | Met | Tyr | Ala | Asp | Leu | Asp | Met | Asp | His | |
| | 195 | | | | | 200 | | | | | 205 | | | | | |
| ccc | gaa | gtc | gtg | acc | gag | ctg | aaa | aac | tgg | ggg | aaa | tgg | tat | gtc | aac | 672 |
| Pro | Glu | Val | Val | Thr | Glu | Leu | Lys | Asn | Trp | Gly | Lys | Trp | Tyr | Val | Asn | |
| | 210 | | | | | 215 | | | | | 220 | | | | | |
| aca | acg | aac | att | gat | ggg | ttc | cgg | ctt | gat | gcc | gtc | aag | cat | att | aag | 720 |
| Thr | Thr | Asn | Ile | Asp | Gly | Phe | Arg | Leu | Asp | Ala | Val | Lys | His | Ile | Lys | |
| 225 | | | | | 230 | | | | | 235 | | | | | 240 | |
| ttc | agt | ttt | ttt | cct | gat | tgg | ttg | tcg | tat | gtg | cgt | tct | cag | act | ggc | 768 |
| Phe | Ser | Phe | Phe | Pro | Asp | Trp | Leu | Ser | Tyr | Val | Arg | Ser | Gln | Thr | Gly | |
| | | | 245 | | | | | 250 | | | | | 255 | | | |
| aag | ccg | cta | ttt | acc | gtc | ggg | gaa | tat | tgg | agc | tat | gac | atc | aac | aag | 816 |
| Lys | Pro | Leu | Phe | Thr | Val | Gly | Glu | Tyr | Trp | Ser | Tyr | Asp | Ile | Asn | Lys | |

-continued

```
                       260                 265                 270
ttg cac aat tac att acg aaa aca gac gga acg atg tct ttg ttt gat         864
Leu His Asn Tyr Ile Thr Lys Thr Asp Gly Thr Met Ser Leu Phe Asp
        275                 280                 285 gcc ccg tta cac aac aaa ttt tat acc gct tcc aaa tca ggg ggc gca         912
Ala Pro Leu His Asn Lys Phe Tyr Thr Ala Ser Lys Ser Gly Gly Ala
    290                 295                 300 ttt gat atg cgc acg tta atg acc aat act ctc atg aaa gat caa ccg         960
Phe Asp Met Arg Thr Leu Met Thr Asn Thr Leu Met Lys Asp Gln Pro
305                 310                 315                 320 aca ttg gcc gtc acc ttc gtt gat aat cat gac acc gaa ccc ggc caa        1008
Thr Leu Ala Val Thr Phe Val Asp Asn His Asp Thr Glu Pro Gly Gln
                325                 330                 335 gcg ctg cag tca tgg gtc gac cca tgg ttc aaa ccg ttg gct tac gcc        1056
Ala Leu Gln Ser Trp Val Asp Pro Trp Phe Lys Pro Leu Ala Tyr Ala
            340                 345                 350 ttt att cta act cgg cag gaa gga tac ccg tgc gtc ttt tat ggt gac        1104
Phe Ile Leu Thr Arg Gln Glu Gly Tyr Pro Cys Val Phe Tyr Gly Asp
        355                 360                 365 tat tat ggc att cca caa tat aac att cct tcg ctg aaa agc aaa atc        1152
Tyr Tyr Gly Ile Pro Gln Tyr Asn Ile Pro Ser Leu Lys Ser Lys Ile
    370                 375                 380 gat ccg ctc ctc atc gcg cgc agg gat tat gct tac gga acg caa cat        1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc        1248
Asp Tyr Leu Asp His Ser Asp Ile Ile Gly Trp Thr Arg Glu Gly Gly
                405                 410                 415 act gaa aaa cca gga tcc gga ctg gcc gca ctg atc acc gat ggg ccg        1296
Thr Glu Lys Pro Gly Ser Gly Leu Ala Ala Leu Ile Thr Asp Gly Pro
            420                 425                 430 gga gga agc aaa tgg atg tac gtt ggc aaa caa cac gct gga aaa gtg        1344
Gly Gly Ser Lys Trp Met Tyr Val Gly Lys Gln His Ala Gly Lys Val
        435                 440                 445 ttc tat gac ctt acc ggc aac cgg agt gac acc gtc acc atc aac agt        1392
Phe Tyr Asp Leu Thr Gly Asn Arg Ser Asp Thr Val Thr Ile Asn Ser
    450                 455                 460 gat gga tgg ggg gaa ttc aaa gtc aat ggc ggt tcg gtt tcg gtt tgg        1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc        1488
Val Pro Arg Lys Thr Thr Val Ser Thr Ile Ala Arg Pro Ile Thr Thr
                485                 490                 495 cga ccg tgg act ggt gaa ttc gtc cgt tgg acc gaa cca cgg ttg gtg        1536
Arg Pro Trp Thr Gly Glu Phe Val Arg Trp Thr Glu Pro Arg Leu Val
            500                 505                 510 gca tgg cct tga                                                        1548
Ala Trp Pro
        515

<210> SEQ ID NO 6
<211> LENGTH: 515
<212> TYPE: PRT
<213> ORGANISM: Bacillus stearothermophilus

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30
```

-continued

```
Leu Ser Ser Leu Gly Ile Thr Ala Leu Trp Leu Pro Pro Ala Tyr Lys
         35                  40                  45

Gly Thr Ser Arg Ser Asp Val Gly Tyr Gly Val Tyr Asp Leu Tyr Asp
 50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445
```

-continued

```
Phe Tyr Asp Leu Thr Gly Asn Arg Ser Asp Thr Val Thr Ile Asn Ser
    450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 7
<211> LENGTH: 1920
<212> TYPE: DNA
<213> ORGANISM: Bacillus licheniformis
<220> FEATURE:
<221> NAME/KEY: CDS
<222> LOCATION: (421)..(1872)

<400> SEQUENCE: 7
cggaagattg aagtacaaa  aataagcaaa agattgtcaa tcatgtcatg agccatgcgg      60
gagacggaaa aatcgtctta atgcacgata tttatgcaac gttcgcagat gctgctgaag    120
agattattaa aaagctgaaa gcaaaaggct atcaattggt aactgtatct cagcttgaag    180
aagtgaagaa gcagagaggc tattgaataa atgagtagaa gcgccatatc ggcgcttttc    240
ttttggaaga aaatataggg aaaatggtac ttgttaaaaa ttcggaatat ttatacaaca    300
tcatatgttt cacattgaaa ggggaggaga atcatgaaac aacaaaaacg gctttacgcc    360
cgattgctga cgctgttatt tgcgctcatc ttcttgctgc ctcattctgc agcagcggcg    420
```

| | | | | | | | | | | | | | | | | |
|---|---|---|---|---|---|---|---|---|---|---|---|---|---|---|---|---|
| gca | aat | ctt | aat | ggg | acg | ctg | atg | cag | tat | ttt | gaa | tgg | tac | atg | ccc | 468 |
| Ala | Asn | Leu | Asn | Gly | Thr | Leu | Met | Gln | Tyr | Phe | Glu | Trp | Tyr | Met | Pro | |
| 1 | | | | 5 | | | | | 10 | | | | | 15 | | |

```
aat gac ggc caa cat tgg agg cgt ttg caa aac gac tcg gca tat ttg      516
Asn Asp Gly Gln His Trp Arg Arg Leu Gln Asn Asp Ser Ala Tyr Leu
            20                  25                  30 gct gaa cac ggt att act gcc gtc tgg att ccc ccg gca tat aag gga      564
Ala Glu His Gly Ile Thr Ala Val Trp Ile Pro Pro Ala Tyr Lys Gly
        35                  40                  45 acg agc caa gcg gat gtg ggc tac ggt gct tac gac ctt tat gat tta      612
Thr Ser Gln Ala Asp Val Gly Tyr Gly Ala Tyr Asp Leu Tyr Asp Leu
    50                  55                  60 ggg gag ttt cat caa aaa ggg acg gtt cgg aca aag tac ggc aca aaa      660
Gly Glu Phe His Gln Lys Gly Thr Val Arg Thr Lys Tyr Gly Thr Lys
65                  70                  75                  80 gga gag ctg caa tct gcg atc aaa agt ctt cat tcc cgc gac att aac      708
Gly Glu Leu Gln Ser Ala Ile Lys Ser Leu His Ser Arg Asp Ile Asn
                85                  90                  95 gtt tac ggg gat gtg gtc atc aac cac aaa ggc ggc gct gat gcg acc      756
Val Tyr Gly Asp Val Val Ile Asn His Lys Gly Gly Ala Asp Ala Thr
            100                 105                 110 gaa gat gta acc gcg gtt gaa gtc gat ccc gct gac cgc aac cgc gta      804
Glu Asp Val Thr Ala Val Glu Val Asp Pro Ala Asp Arg Asn Arg Val
        115                 120                 125 att tca gga gaa cac cta att aaa gcc tgg aca cat ttt cat ttt ccg      852
Ile Ser Gly Glu His Leu Ile Lys Ala Trp Thr His Phe His Phe Pro
    130                 135                 140 ggg cgc ggc agc aca tac agc gat ttt aaa tgg cat tgg tac cat ttt      900
Gly Arg Gly Ser Thr Tyr Ser Asp Phe Lys Trp His Trp Tyr His Phe
145                 150                 155                 160
```

```
                                                          -continued gac gga acc gat tgg gac gag tcc cga aag ctg aac cgc atc tat aag         948
Asp Gly Thr Asp Trp Asp Glu Ser Arg Lys Leu Asn Arg Ile Tyr Lys
            165                 170                 175 ttt caa gga aag gct tgg gat tgg gaa gtt tcc aat gaa aac ggc aac         996
Phe Gln Gly Lys Ala Trp Asp Trp Glu Val Ser Asn Glu Asn Gly Asn
        180                 185                 190 tat gat tat ttg atg tat gcc gac atc gat tat gac cat cct gat gtc        1044
Tyr Asp Tyr Leu Met Tyr Ala Asp Ile Asp Tyr Asp His Pro Asp Val
    195                 200                 205 gca gca gaa att aag aga tgg ggc act tgg tat gcc aat gaa ctg caa        1092
Ala Ala Glu Ile Lys Arg Trp Gly Thr Trp Tyr Ala Asn Glu Leu Gln
210                 215                 220 ttg gac ggt ttc cgt ctt gat gct gtc aaa cac att aaa ttt tct ttt        1140
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg        1188
Leu Arg Asp Trp Val Asn His Val Arg Glu Lys Thr Gly Lys Glu Met
                245                 250                 255 ttt acg gta gct gaa tat tgg cag aat gac ttg ggc gcg ctg gaa aac        1236
Phe Thr Val Ala Glu Tyr Trp Gln Asn Asp Leu Gly Ala Leu Glu Asn
            260                 265                 270 tat ttg aac aaa aca aat ttt aat cat tca gtg ttt gac gtg ccg ctt        1284
Tyr Leu Asn Lys Thr Asn Phe Asn His Ser Val Phe Asp Val Pro Leu
        275                 280                 285 cat tat cag ttc cat gct gca tcg aca cag gga ggc ggc tat gat atg        1332
His Tyr Gln Phe His Ala Ala Ser Thr Gln Gly Gly Gly Tyr Asp Met
    290                 295                 300 agg aaa ttg ctg aac ggt acg gtc gtt tcc aag cat ccg ttg aaa tcg        1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag        1428
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc        1476
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg        1524
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att        1572
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat        1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac        1668
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc        1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca        1764
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg        1812
Trp His Asp Ile Thr Gly Asn Arg Ser Glu Pro Val Val Ile Asn Ser
    450                 455                 460 gaa ggc tgg gga gag ttt cac gta aac ggc ggg tcg gtt tca att tat        1860
Glu Gly Trp Gly Glu Phe His Val Asn Gly Gly Ser Val Ser Ile Tyr
```

```
                465                 470                 475                 480
gtt caa aga tag aagagcagag aggacggatt tcctgaagga aatccgtttt                    1912
Val Gln Arg tttatttt                                                                      1920

<210> SEQ ID NO 8
<211> LENGTH: 483
<212> TYPE: PRT
<213> ORGANISM: Bacillus licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
```

-continued

```
                    340                 345                 350
Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 2084
<212> TYPE: DNA
<213> ORGANISM: Bacillus amyloliquefaciens
<220> FEATURE:
<221> NAME/KEY: CDS
<222> LOCATION: (343)..(1794)

<400> SEQUENCE: 9
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtattttta tgctgtccag actgtccgct gtgtaaaaat aaggaataaa     180 gggggttgt tattattta ctgatatgta aatataatt tgtataagaa aatgagaggg      240
agaggaaaca tgattcaaaa acgaaagcgg acagtttcgt tcagacttgt gcttatgtgc     300
acgctgttat ttgtcagttt gccgattaca aaacatcag cc gta aat ggc acg          354
                                              Val Asn Gly Thr
                                                1 ctg atg cag tat ttt gaa tgg tat acg ccg aac gac ggc cag cat tgg      402
Leu Met Gln Tyr Phe Glu Trp Tyr Thr Pro Asn Asp Gly Gln His Trp
 5              10                  15                  20 aaa cga ttg cag aat gat gcg gaa cat tta tcg gat atc gga atc act      450
Lys Arg Leu Gln Asn Asp Ala Glu His Leu Ser Asp Ile Gly Ile Thr
                25                  30                  35 gcc gtc tgg att cct ccc gca tac aaa gga ttg agc caa tcc gat aac      498
Ala Val Trp Ile Pro Pro Ala Tyr Lys Gly Leu Ser Gln Ser Asp Asn
            40                  45                  50 gga tac gga cct tat gat ttg tat gat tta gga gaa ttc cag caa aaa      546
Gly Tyr Gly Pro Tyr Asp Leu Tyr Asp Leu Gly Glu Phe Gln Gln Lys
        55                  60                  65 ggg acg gtc aga acg aaa tac ggc aca aaa tca gag ctt caa gat gcg      594
Gly Thr Val Arg Thr Lys Tyr Gly Thr Lys Ser Glu Leu Gln Asp Ala
    70                  75                  80 atc ggc tca ctg cat tcc cgg aac gtc caa gta tac gga gat gtg gtt      642
Ile Gly Ser Leu His Ser Arg Asn Val Gln Val Tyr Gly Asp Val Val
85                  90                  95                 100 ttg aat cat aag gct ggt gct gat gca aca gaa gat gta act gcc gtc      690
Leu Asn His Lys Ala Gly Ala Asp Ala Thr Glu Asp Val Thr Ala Val
```

-continued

|     |     |     |     | 105 |     |     |     | 110 |     |     |     | 115 |     |     |      |
|-----|-----|-----|-----|-----|-----|-----|-----|-----|-----|-----|-----|-----|-----|-----|------|
| gaa | gtc | aat | ccg | gcc | aat | aga | aat | cag | gaa | act | tcg | gag | gaa | tat | caa  |
| Glu | Val | Asn | Pro | Ala | Asn | Arg | Asn | Gln | Glu | Thr | Ser | Glu | Glu | Tyr | Gln  |
|     |     |     | 120 |     |     |     |     | 125 |     |     |     |     |     | 130 |      |

738 atc aaa gcg tgg acg gat ttt cgt ttt ccg ggc cgt gga aac acg tac      786
Ile Lys Ala Trp Thr Asp Phe Arg Phe Pro Gly Arg Gly Asn Thr Tyr
            135                     140                 145 agt gat ttt aaa tgg cat tgg tat cat ttc gac gga gcg gac tgg gat      834
Ser Asp Phe Lys Trp His Trp Tyr His Phe Asp Gly Ala Asp Trp Asp
        150                     155                 160 gaa tcc cgg aag atc agc cgc atc ttt aag ttt cgt ggg gaa gga aaa      882
Glu Ser Arg Lys Ile Ser Arg Ile Phe Lys Phe Arg Gly Glu Gly Lys
165                     170                     175                 180 gcg tgg gat tgg gaa gta tca agt gaa aac ggc aac tat gac tat tta      930
Ala Trp Asp Trp Glu Val Ser Ser Glu Asn Gly Asn Tyr Asp Tyr Leu
                    185                     190                 195 atg tat gct gat gtt gac tac gac cac cct gat gtc gtg gca gag aca      978
Met Tyr Ala Asp Val Asp Tyr Asp His Pro Asp Val Val Ala Glu Thr
                200                     205                     210 aaa aaa tgg ggt atc tgg tat gcg aat gaa ctg tca tta gac ggc ttc     1026
Lys Lys Trp Gly Ile Trp Tyr Ala Asn Glu Leu Ser Leu Asp Gly Phe
            215                     220                     225 cgt att gat gcc gcc aaa cat att aaa ttt tca ttt ctg cgt gat tgg     1074
Arg Ile Asp Ala Ala Lys His Ile Lys Phe Ser Phe Leu Arg Asp Trp
        230                     235                     240 gtt cag gcg gtc aga cag gcg acg gga aaa gaa atg ttt acg gtt gcg     1122
Val Gln Ala Val Arg Gln Ala Thr Gly Lys Glu Met Phe Thr Val Ala
245                     250                     255                 260 gag tat tgg cag aat aat gcc ggg aaa ctc gaa aac tac ttg aat aaa     1170
Glu Tyr Trp Gln Asn Asn Ala Gly Lys Leu Glu Asn Tyr Leu Asn Lys
                    265                     270                 275 aca agc ttt aat caa tcc gtg ttt gat gtt ccg ctt cat ttc aat tta     1218
Thr Ser Phe Asn Gln Ser Val Phe Asp Val Pro Leu His Phe Asn Leu
                280                     285                     290 cag gcg gct tcc tca caa gga ggc gga tat gat atg agg cgt ttg ctg     1266
Gln Ala Ala Ser Ser Gln Gly Gly Gly Tyr Asp Met Arg Arg Leu Leu
            295                     300                     305 gac ggt acc gtt gtg tcc agg cat ccg gaa aag gcg gtt aca ttt gtt     1314
Asp Gly Thr Val Val Ser Arg His Pro Glu Lys Ala Val Thr Phe Val
        310                     315                     320 gaa aat cat gac aca cag ccg gga cag tca ttg gaa tcg aca gtc caa     1362
Glu Asn His Asp Thr Gln Pro Gly Gln Ser Leu Glu Ser Thr Val Gln
325                     330                     335                 340 act tgg ttt aaa ccg ctt gca tac gcc ttt att ttg aca aga gaa tcc     1410
Thr Trp Phe Lys Pro Leu Ala Tyr Ala Phe Ile Leu Thr Arg Glu Ser
                    345                     350                 355 ggt tat cct cag gtg ttc tat ggg gat atg tac ggg aca aaa ggg aca     1458
Gly Tyr Pro Gln Val Phe Tyr Gly Asp Met Tyr Gly Thr Lys Gly Thr
                360                     365                     370 tcg cca aag gaa att ccc tca ctg aaa gat aat ata gag ccg att tta     1506
Ser Pro Lys Glu Ile Pro Ser Leu Lys Asp Asn Ile Glu Pro Ile Leu
            375                     380                     385 aaa gcg cgt aag gag tac gca tac ggg ccc cag cac gat tat att gac     1554
Lys Ala Arg Lys Glu Tyr Ala Tyr Gly Pro Gln His Asp Tyr Ile Asp
        390                     395                     400 cac ccg gat gtg atc gga tgg acg agg gaa ggt gac agc tcc gcc gcc     1602
His Pro Asp Val Ile Gly Trp Thr Arg Glu Gly Asp Ser Ser Ala Ala
405                     410                     415                 420 aaa tca ggt ttg gcc gct tta atc acg gac gga ccc ggc gga tca aag     1650

```
                                            -continued

Lys Ser Gly Leu Ala Ala Leu Ile Thr Asp Gly Pro Gly Gly Ser Lys
                425                 430                 435 cgg atg tat gcc ggc ctg aaa aat gcc ggc gag aca tgg tat gac ata      1698
Arg Met Tyr Ala Gly Leu Lys Asn Ala Gly Glu Thr Trp Tyr Asp Ile
                440                 445                 450 acg ggc aac cgt tca gat act gta aaa atc gga tct gac ggc tgg gga      1746
Thr Gly Asn Arg Ser Asp Thr Val Lys Ile Gly Ser Asp Gly Trp Gly
                455                 460                 465 gag ttt cat gta aac gat ggg tcc gtc tcc att tat gtt cag aaa taa      1794
Glu Phe His Val Asn Asp Gly Ser Val Ser Ile Tyr Val Gln Lys
                470                 475                 480 ggtaataaaa aaacacctcc aagctgagtg cgggtatcag cttggaggtg cgtttatttt    1854
ttcagccgta tgacaaggtc ggcatcaggt gtgacaaata cggtatgctg gctgtcatag    1914
gtgacaaatc cgggttttgc gccgtttggc ttttcacat gtctgatttt tgtataatca     1974
acaggcacgg agccggaatc tttcgccttg gaaaaataag cggcgatcgt agctgcttcc    2034
aatatggatt gttcatcggg atcgctgctt ttaatcacaa cgtgggatcc               2084

<210> SEQ ID NO 10
<211> LENGTH: 483
<212> TYPE: PRT
<213> ORGANISM: Bacillus amyloliquefaciens

<400> SEQUENCE: 10

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
        50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
                100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
                180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
        210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
```

```
                        245                 250                 255
Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
            290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
            370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 11
<211> LENGTH: 1458
<212> TYPE: DNA
<213> ORGANISM: Bacillus species
<220> FEATURE:
<221> NAME/KEY: CDS
<222> LOCATION: (1)..(1458)

<400> SEQUENCE: 11 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt      96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg     144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat     192
Lys Gly Ala Ser Gln Asn Asp Val Gly Tyr Gly Ala Tyr Asp Leu Tyr
    50                  55                  60 gat tta gga gaa ttc aat caa aaa gga acc att cgt aca aaa tat gga     240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga     288
Thr Arg Asn Gln Leu Gln Ala Ala Val Asn Ala Leu Lys Ser Asn Gly
```

-continued

|   |   | 85 |   |   |   | 90 |   |   |   | 95 |   |   |   |
|---|---|---|---|---|---|---|---|---|---|---|---|---|---|

```
att caa gtg tat ggc gat gtt gta atg aat cat aaa ggg gga gca gac    336
Ile Gln Val Tyr Gly Asp Val Val Met Asn His Lys Gly Gly Ala Asp
            100                 105                 110 gct acc gaa atg gtt agg gca gtt gaa gta aac ccg aat aat aga aat    384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac    432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat    480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga    528
His Phe Asp Gly Val Asp Trp Asp Gln Ser Arg Lys Leu Asn Asn Arg
                165                 170                 175 att tat aaa ttt aga ggt gat gga aaa ggg tgg gat tgg gaa gtc gat    576
Ile Tyr Lys Phe Arg Gly Asp Gly Lys Gly Trp Asp Trp Glu Val Asp
            180                 185                 190 aca gaa aac ggt aac tat gat tac cta atg tat gca gat att gac atg    624
Thr Glu Asn Gly Asn Tyr Asp Tyr Leu Met Tyr Ala Asp Ile Asp Met
        195                 200                 205 gat cac cca gag gta gtg aat gag cta aga aat tgg ggt gtt tgg tat    672
Asp His Pro Glu Val Val Asn Glu Leu Arg Asn Trp Gly Val Trp Tyr
    210                 215                 220 acg aat aca tta ggc ctt gat ggt ttt aga ata gat gca gta aaa cat    720
Thr Asn Thr Leu Gly Leu Asp Gly Phe Arg Ile Asp Ala Val Lys His
225                 230                 235                 240 ata aaa tac agc ttt act cgt gat tgg att aat cat gtt aga agt gca    768
Ile Lys Tyr Ser Phe Thr Arg Asp Trp Ile Asn His Val Arg Ser Ala
                245                 250                 255 act ggc aaa aat atg ttt gcg gtt gcg gaa ttt tgg aaa aat gat tta    816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc    864
Gly Ala Ile Glu Asn Tyr Leu Asn Lys Thr Asn Trp Asn His Ser Val
        275                 280                 285 ttt gat gtt ccg ctg cac tat aac ctc tat aat gct tca aaa agc gga    912
Phe Asp Val Pro Leu His Tyr Asn Leu Tyr Asn Ala Ser Lys Ser Gly
    290                 295                 300 ggg aat tat gat atg agg caa ata ttt aat ggt aca gtc gtg caa aga    960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct    1008
His Pro Met His Ala Val Thr Phe Val Asp Asn His Asp Ser Gln Pro
                325                 330                 335 gaa gaa gct tta gag tct ttt gtt gaa gaa tgg ttc aaa cca tta gcg    1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat    1104
Tyr Ala Leu Thr Leu Thr Arg Glu Gln Gly Tyr Pro Ser Val Phe Tyr
        355                 360                 365 gga gat tat tat ggc att cca acg cat ggt gta cca gcg atg aaa tcg    1152
Gly Asp Tyr Tyr Gly Ile Pro Thr His Gly Val Pro Ala Met Lys Ser
    370                 375                 380 aaa att gac ccg att cta gaa gcg cgt caa aag tat gca tat gga aga    1200
Lys Ile Asp Pro Ile Leu Glu Ala Arg Gln Lys Tyr Ala Tyr Gly Arg
385                 390                 395                 400 caa aat gac tac tta gac cat cat aat atc atc ggt tgg aca cgt gaa    1248
```

```
                Gln Asn Asp Tyr Leu Asp His His Asn Ile Ile Gly Trp Thr Arg Glu
                                405                 410                 415 ggg aat aca gca cac ccc aac tcc ggt tta gct act atc atg tcc gat         1296
Gly Asn Thr Ala His Pro Asn Ser Gly Leu Ala Thr Ile Met Ser Asp
            420                 425                 430 ggg gca gga gga aat aag tgg atg ttt gtt ggg cgt aat aaa gct ggt         1344
Gly Ala Gly Gly Asn Lys Trp Met Phe Val Gly Arg Asn Lys Ala Gly
        435                 440                 445 caa gtt tgg acc gat atc act gga aat cgt gca ggt act gtt acg att         1392
Gln Val Trp Thr Asp Ile Thr Gly Asn Arg Ala Gly Thr Val Thr Ile
    450                 455                 460 aat gct gat gga tgg ggt aat ttt tct gta aat gga gga tca gtt tct         1440
Asn Ala Asp Gly Trp Gly Asn Phe Ser Val Asn Gly Gly Ser Val Ser
465                 470                 475                 480 att tgg gta aac aaa taa                                                 1458
Ile Trp Val Asn Lys
                485

<210> SEQ ID NO 12
<211> LENGTH: 485
<212> TYPE: PRT
<213> ORGANISM: Bacillus species

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255
```

```
Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
        290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 13
<211> LENGTH: 197
<212> TYPE: PRT
<213> ORGANISM: Bacillus species

<400> SEQUENCE: 13

Phe Asp Val Pro Leu His Tyr Asn Leu Tyr Asn Ala Ser Lys Ser Gly
1               5                   10                  15

Gly Asn Tyr Asp Met Arg Asn Ile Phe Asn Gly Thr Val Val Gln Arg
                20                  25                  30

His Pro Ser His Ala Val Thr Phe Val Asp Asn His Asp Ser Gln Pro
            35                  40                  45

Glu Glu Ala Leu Glu Ser Phe Val Glu Glu Trp Phe Lys Pro Leu Ala
        50                  55                  60

Tyr Ala Leu Thr Leu Thr Arg Glu Gln Gly Tyr Pro Ser Val Phe Tyr
65                  70                  75                  80

Gly Asp Tyr Tyr Gly Ile Pro Thr His Gly Val Pro Ala Met Arg Ser
                85                  90                  95

Lys Ile Asp Pro Ile Leu Glu Ala Arg Gln Lys Tyr Ala Tyr Gly Lys
            100                 105                 110

Gln Asn Asp Tyr Leu Asp His His Asn Ile Ile Gly Trp Thr Arg Glu
        115                 120                 125

Gly Asn Thr Ala His Pro Asn Ser Gly Leu Ala Thr Ile Met Ser Asp
        130                 135                 140
```

Gly Ala Gly Gly Ser Lys Trp Met Phe Val Gly Arg Asn Lys Ala Gly
145                 150                 155                 160

Gln Val Trp Ser Asp Ile Thr Gly Asn Arg Thr Gly Thr Val Thr Ile
                165                 170                 175

Asn Ala Asp Gly Trp Gly Asn Phe Ser Val Asn Gly Gly Ser Val Ser
            180                 185                 190

Ile Trp Val Asn Lys
        195

<210> SEQ ID NO 14
<211> LENGTH: 24
<212> TYPE: DNA
<213> ORGANISM: Artificial Sequence
<220> FEATURE:
<223> OTHER INFORMATION: Synthetic construct

<400> SEQUENCE: 14
cgattgctga cgctgttatt tgcg                                          24

<210> SEQ ID NO 15
<211> LENGTH: 19
<212> TYPE: DNA
<213> ORGANISM: Artificial Sequence
<220> FEATURE:
<223> OTHER INFORMATION: Synthetic construct

<400> SEQUENCE: 15
gatcacccgc gataccgtc                                                19

<210> SEQ ID NO 16
<211> LENGTH: 31
<212> TYPE: DNA
<213> ORGANISM: Artificial Sequence
<220> FEATURE:
<223> OTHER INFORMATION: Synthetic construct

<400> SEQUENCE: 16
gaatgtatgt cggccggcaa aacgccggtg a                                  31

<210> SEQ ID NO 17
<211> LENGTH: 30
<212> TYPE: DNA
<213> ORGANISM: Artificial Sequence
<220> FEATURE:
<223> OTHER INFORMATION: Synthetic construct

<400> SEQUENCE: 17
gccgccgctg ctgcagaatg aggcagcaag                                    30

<210> SEQ ID NO 18
<211> LENGTH: 48
<212> TYPE: DNA
<213> ORGANISM: Artificial Sequence
<220> FEATURE:
<223> OTHER INFORMATION: Synthetic construct

<400> SEQUENCE: 18
cccgaaagct gaaccgcatc tataggtttc aagggaagac ttgggatt                48

<210> SEQ ID NO 19
<211> LENGTH: 23
<212> TYPE: DNA
<213> ORGANISM: Artificial Sequence
<220> FEATURE:

-continued

<223> OTHER INFORMATION: Synthetic construct

<400> SEQUENCE: 19
aggatggtca taatcaaagt cgg                                              23

<210> SEQ ID NO 20
<211> LENGTH: 52
<212> TYPE: DNA
<213> ORGANISM: Artificial Sequence
<220> FEATURE:
<223> OTHER INFORMATION: Synthetic construct

<400> SEQUENCE: 20
ccgactttga ttatgaccat cctgttgtcg tagcagagat taagagatgg gg              52

<210> SEQ ID NO 21
<211> LENGTH: 45
<212> TYPE: DNA
<213> ORGANISM: Artificial Sequence
<220> FEATURE:
<223> OTHER INFORMATION: Synthetic construct

<400> SEQUENCE: 21
cgacaatgtc atggtggtcg aaaaaatcat gctgtgctcc gtacg                      45

<210> SEQ ID NO 22
<211> LENGTH: 23
<212> TYPE: DNA
<213> ORGANISM: Artificial Sequence
<220> FEATURE:
<223> OTHER INFORMATION: Synthetic construct

<400> SEQUENCE: 22
tttcgaccac catgacattg tcg                                              23

<210> SEQ ID NO 23
<211> LENGTH: 24
<212> TYPE: DNA
<213> ORGANISM: Artificial Sequence
<220> FEATURE:
<223> OTHER INFORMATION: Synthetic construct

<400> SEQUENCE: 23
tatagatgcg gttcagcttt cggg                                             24

<210> SEQ ID NO 24
<211> LENGTH: 1650
<212> TYPE: DNA
<213> ORGANISM: Bacillus species

<400> SEQUENCE: 24
cttgaatcat tatttaaagc tggttatgat atatgtaagc gttatcatta aaaggaggta      60
tttgatgaaa agatgggtag tagcaatgct ggcagtgtta ttttatttc cttcggtagt      120 agttgcagat ggcttgaatg gaacgatgat gcagtattat gagtggcatc tagagaatga    180
tgggcaacac tggaatcggt tgcatgatga tgccgaagct ttaagtaatg cgggtattac    240
agctatttgg ataccccag cctacaaagg aaatagtcag gctgatgttg ggtatggtgc      300
atacgacctt tatgatttag gggagtttaa tcaaaaaggt accgttcgaa cgaaatacgg    360
gacaaaggct cagcttgagc gagctatagg gtccctaaag tcgaatgata tcaatgttta    420 tgggatgtc gtaatgaatc ataaattagg agctgatttc acggaggcag tgcaagctgt      480
tcaagtaaat ccttcgaacc gttggcagga tatttcaggt gtctacacga ttgatgcatg    540

```
gacgggattt gactttccag ggcgcaacaa tgcctattcc gattttaaat ggagatggtt    600
ccatttttaat ggcgttgact gggatcaacg ctatcaagaa aaccatcttt ttcgctttgc   660
aaatacgaac tggaactggc gagtggatga agagaatggt aattatgact atttattagg   720
atcgaacatt gactttagcc acccagaggt tcaagaggaa ttaaaggatt ggggagctg    780
gtttacggat gagctagatt tagatgggta tcgattggat gctattaagc atattccatt   840
ctggtatacg tcagattggg ttaggcatca gcgaagtgaa gcagaccaag atttatttgt   900
cgtaggggag tattgaagg atgacgtagg tgctctcgaa tttttatttag atgaaatgaa   960
ttgggagatg tctctattcg atgttccgct caattataat ttttaccggg cttcaaagca   1020
aggcggaagc tatgatatgc gtaatatttt acgaggatct ttagtagaag cacatccgat   1080
tcatgcagtt acgtttgttg ataatcatga tactcagcca ggagagtcat tagaatcatg   1140
ggtcgctgat tggtttaagc cacttgctta tgcgacaatc ttgacgcgtg aaggtggtta   1200
tccaaatgta ttttacggtg actactatgg gattcctaac gataacattt cagctaagaa   1260
ggatatgatt gatgagttgc ttgatgcacg tcaaaattac gcatatggca cacaacatga   1320
ctattttgat cattgggata tcgttggatg gacaagagaa ggtacatcct cacgtcctaa   1380
ttcgggtctt gctactatta tgtccaatgg tcctggagga tcaaaatgga tgtacgtagg   1440
acagcaacat gcaggacaaa cgtggacaga tttaactggc aatcacgcgg cgtcggttac   1500
gattaatggt gatggctggg gcgaattctt tacaaatgga ggatctgtat ccgtgtatgt   1560
gaaccaataa taaaaagcct tgagaaggga ttcctcccta actcaaggct ttctttatgt   1620
cgtttagctc aacgcttcta cgaagcttta                                    1650

<210> SEQ ID NO 25
<211> LENGTH: 501
<212> TYPE: PRT
<213> ORGANISM: Bacillus species

<400> SEQUENCE: 25

Met Lys Arg Trp Val Val Ala Met Leu Ala Val Leu Phe Leu Phe Pro
1               5                   10                  15

Ser Val Val Ala Asp Gly Leu Asn Gly Thr Met Met Gln Tyr Tyr
            20                  25                  30

Glu Trp His Leu Glu Asn Asp Gly Gln His Trp Asn Arg Leu His Asp
        35                  40                  45

Asp Ala Glu Ala Leu Ser Asn Ala Gly Ile Thr Ala Ile Trp Ile Pro
    50                  55                  60

Pro Ala Tyr Lys Gly Asn Ser Gln Ala Asp Val Gly Tyr Gly Ala Tyr
65                  70                  75                  80

Asp Leu Tyr Asp Leu Gly Glu Phe Asn Gln Lys Gly Thr Val Arg Thr
                85                  90                  95

Lys Tyr Gly Thr Lys Ala Gln Leu Glu Arg Ala Ile Gly Ser Leu Lys
            100                 105                 110

Ser Asn Asp Ile Asn Val Tyr Gly Asp Val Val Met Asn His Lys Leu
        115                 120                 125

Gly Ala Asp Phe Thr Glu Ala Val Gln Ala Val Gln Val Asn Pro Ser
    130                 135                 140

Asn Arg Trp Gln Asp Ile Ser Gly Val Tyr Thr Ile Asp Ala Trp Thr
145                 150                 155                 160

Gly Phe Asp Phe Pro Gly Arg Asn Asn Ala Tyr Ser Asp Phe Lys Trp
                165                 170                 175
```

```
Arg Trp Phe His Phe Asn Gly Val Asp Trp Asp Gln Arg Tyr Gln Glu
            180                 185                 190

Asn His Leu Phe Arg Phe Ala Asn Thr Asn Trp Asn Trp Arg Val Asp
            195                 200                 205

Glu Glu Asn Gly Asn Tyr Asp Tyr Leu Leu Gly Ser Asn Ile Asp Phe
            210                 215                 220

Ser His Pro Glu Val Gln Glu Leu Lys Asp Trp Gly Ser Trp Phe
225                 230                 235                 240

Thr Asp Glu Leu Asp Leu Asp Gly Tyr Arg Leu Asp Ala Ile Lys His
                245                 250                 255

Ile Pro Phe Trp Tyr Thr Ser Asp Trp Val Arg His Gln Arg Ser Glu
            260                 265                 270

Ala Asp Gln Asp Leu Phe Val Val Gly Glu Tyr Trp Lys Asp Asp Val
            275                 280                 285

Gly Ala Leu Glu Phe Tyr Leu Asp Glu Met Asn Trp Glu Met Ser Leu
            290                 295                 300

Phe Asp Val Pro Leu Asn Tyr Asn Phe Tyr Arg Ala Ser Lys Gln Gly
305                 310                 315                 320

Gly Ser Tyr Asp Met Arg Asn Ile Leu Arg Gly Ser Leu Val Glu Ala
                325                 330                 335

His Pro Ile His Ala Val Thr Phe Val Asp Asn His Asp Thr Gln Pro
            340                 345                 350

Gly Glu Ser Leu Glu Ser Trp Val Ala Asp Trp Phe Lys Pro Leu Ala
            355                 360                 365

Tyr Ala Thr Ile Leu Thr Arg Glu Gly Gly Tyr Pro Asn Val Phe Tyr
            370                 375                 380

Gly Asp Tyr Tyr Gly Ile Pro Asn Asp Asn Ile Ser Ala Lys Lys Asp
385                 390                 395                 400

Met Ile Asp Glu Leu Leu Asp Ala Arg Gln Asn Tyr Ala Tyr Gly Thr
                405                 410                 415

Gln His Asp Tyr Phe Asp His Trp Asp Ile Val Gly Trp Thr Arg Glu
            420                 425                 430

Gly Thr Ser Ser Arg Pro Asn Ser Gly Leu Ala Thr Ile Met Ser Asn
            435                 440                 445

Gly Pro Gly Gly Ser Lys Trp Met Tyr Val Gly Gln Gln His Ala Gly
            450                 455                 460

Gln Thr Trp Thr Asp Leu Thr Gly Asn His Ala Ala Ser Val Thr Ile
465                 470                 475                 480

Asn Gly Asp Gly Trp Gly Glu Phe Phe Thr Asn Gly Gly Ser Val Ser
                485                 490                 495

Val Tyr Val Asn Gln
            500

<210> SEQ ID NO 26
<211> LENGTH: 1745
<212> TYPE: DNA
<213> ORGANISM: Bacillus species
<220> FEATURE:
<221> NAME/KEY: CDS
<222> LOCATION: (190)..(1692)
<220> FEATURE:
<221> NAME/KEY: sig_peptide
<222> LOCATION: (190)..(253)
<220> FEATURE:
<221> NAME/KEY: mat_peptide
<222> LOCATION: (253)..()
```

<400> SEQUENCE: 26

```
aactaagtaa catcgattca ggataaaagt atgcgaaacg atgcgcaaaa ctgcgcaact      60
actagcactc ttcagggact aaaccacctt ttttccaaaa atgacatcat ataaacaaat     120
ttgtctacca atcactattt aaagctgttt atgatatatg taagcgttat cattaaaagg     180 aggtatttg atg aga aga tgg gta gta gca atg ttg gca gtg tta ttt tta    231
         Met Arg Arg Trp Val Val Ala Met Leu Ala Val Leu Phe Leu
             -20             -15                 -10 ttt cct tcg gta gta gtt gca gat gga ttg aac ggt acg atg atg cag      279
Phe Pro Ser Val Val Val Ala Asp Gly Leu Asn Gly Thr Met Met Gln
         -5              -1  1               5 tat tat gag tgg cat ttg gaa aac gac ggg cag cat tgg aat cgg ttg      327
Tyr Tyr Glu Trp His Leu Glu Asn Asp Gly Gln His Trp Asn Arg Leu
10              15                  20                  25 cac gat gat gcc gca gct ttg agt gat gct ggt att aca gct att tgg      375
His Asp Asp Ala Ala Ala Leu Ser Asp Ala Gly Ile Thr Ala Ile Trp
                30                  35                  40 att ccg cca gcc tac aaa ggt aat agt cag gcg gat gtt ggg tac ggt      423
Ile Pro Pro Ala Tyr Lys Gly Asn Ser Gln Ala Asp Val Gly Tyr Gly
                45                  50                  55 gca tac gat ctt tat gat tta gga gag ttc aat caa aag ggt act gtt      471
Ala Tyr Asp Leu Tyr Asp Leu Gly Glu Phe Asn Gln Lys Gly Thr Val
            60                  65                  70 cga acg aaa tac gga act aag gca cag ctt gaa cga gct att ggg tcc      519
Arg Thr Lys Tyr Gly Thr Lys Ala Gln Leu Glu Arg Ala Ile Gly Ser
75                  80                  85 ctt aaa tct aat gat atc aat gta tac gga gat gtc gtg atg aat cat      567
Leu Lys Ser Asn Asp Ile Asn Val Tyr Gly Asp Val Val Met Asn His
90                  95                  100                 105 aaa atg gga gct gat ttt acg gag gca gtg caa gct gtt caa gta aat      615
Lys Met Gly Ala Asp Phe Thr Glu Ala Val Gln Ala Val Gln Val Asn
                110                 115                 120 cca acg aat cgt tgg cag gat att tca ggt gcc tac acg att gat gcg      663
Pro Thr Asn Arg Trp Gln Asp Ile Ser Gly Ala Tyr Thr Ile Asp Ala
                125                 130                 135 tgg acg ggt ttc gac ttt tca ggg cgt aac aac gcc tat tca gat ttt      711
Trp Thr Gly Phe Asp Phe Ser Gly Arg Asn Asn Ala Tyr Ser Asp Phe
            140                 145                 150 aag tgg aga tgg ttc cat ttt aat ggt gtt gac tgg gat cag cgc tat      759
Lys Trp Arg Trp Phe His Phe Asn Gly Val Asp Trp Asp Gln Arg Tyr
        155                 160                 165 caa gaa aat cat att ttc cgc ttt gca aat acg aac tgg aac tgg cga      807
Gln Glu Asn His Ile Phe Arg Phe Ala Asn Thr Asn Trp Asn Trp Arg
170                 175                 180                 185 gtg gat gaa gag aac ggt aat tat gat tac ctg tta gga tcg aat atc      855
Val Asp Glu Glu Asn Gly Asn Tyr Asp Tyr Leu Leu Gly Ser Asn Ile
                190                 195                 200 gac ttt agt cat cca gaa gta caa gat gag ttg aag gat tgg ggt agc      903
Asp Phe Ser His Pro Glu Val Gln Asp Glu Leu Lys Asp Trp Gly Ser
            205                 210                 215 tgg ttt acc gat gag tta gat ttg gat ggt tat cgt tta gat gct att      951
Trp Phe Thr Asp Glu Leu Asp Leu Asp Gly Tyr Arg Leu Asp Ala Ile
        220                 225                 230 aaa cat att cca ttc tgg tat aca tct gat tgg gtt cgg cat cag cgc      999
Lys His Ile Pro Phe Trp Tyr Thr Ser Asp Trp Val Arg His Gln Arg
235                 240                 245 aac gaa gca gat caa gat tta ttt gtc gta ggg gaa tat tgg aag gat     1047
Asn Glu Ala Asp Gln Asp Leu Phe Val Val Gly Glu Tyr Trp Lys Asp
250                 255                 260                 265
```

| | | |
|---|---|---|
| gac gta ggt gct ctc gaa ttt tat tta gat gaa atg aat tgg gag atg<br>Asp Val Gly Ala Leu Glu Phe Tyr Leu Asp Glu Met Asn Trp Glu Met<br>270 275 280 | | 1095 |
| tct cta ttc gat gtt cca ctt aat tat aat ttt tac cgg gct tca caa<br>Ser Leu Phe Asp Val Pro Leu Asn Tyr Asn Phe Tyr Arg Ala Ser Gln<br>285 290 295 | | 1143 |
| caa ggt gga agc tat gat atg cgt aat att tta cga gga tct tta gta<br>Gln Gly Gly Ser Tyr Asp Met Arg Asn Ile Leu Arg Gly Ser Leu Val<br>300 305 310 | | 1191 |
| gaa gcg cat ccg atg cat gca gtt acg ttt gtt gat aat cat gat act<br>Glu Ala His Pro Met His Ala Val Thr Phe Val Asp Asn His Asp Thr<br>315 320 325 | | 1239 |
| cag cca ggg gag tca tta gag tca tgg gtt gct gat tgg ttt aag cca<br>Gln Pro Gly Glu Ser Leu Glu Ser Trp Val Ala Asp Trp Phe Lys Pro<br>330 335 340 345 | | 1287 |
| ctt gct tat gcg aca att ttg acg cgt gaa ggt ggt tat cca aat gta<br>Leu Ala Tyr Ala Thr Ile Leu Thr Arg Glu Gly Gly Tyr Pro Asn Val<br>350 355 360 | | 1335 |
| ttt tac ggt gat tac tat ggg att cct aac gat aac att tca gct aaa<br>Phe Tyr Gly Asp Tyr Tyr Gly Ile Pro Asn Asp Asn Ile Ser Ala Lys<br>365 370 375 | | 1383 |
| aaa gat atg att gat gag ctg ctt gat gca cgt caa aat tac gca tat<br>Lys Asp Met Ile Asp Glu Leu Leu Asp Ala Arg Gln Asn Tyr Ala Tyr<br>380 385 390 | | 1431 |
| ggc acg cag cat gac tat ttt gat cat tgg gat gtt gta gga tgg act<br>Gly Thr Gln His Asp Tyr Phe Asp His Trp Asp Val Val Gly Trp Thr<br>395 400 405 | | 1479 |
| agg gaa gga tct tcc tcc aga cct aat tca ggc ctt gcg act att atg<br>Arg Glu Gly Ser Ser Ser Arg Pro Asn Ser Gly Leu Ala Thr Ile Met<br>410 415 420 425 | | 1527 |
| tcg aat gga cct ggt ggt tcc aag tgg atg tat gta gga cgt cag aat<br>Ser Asn Gly Pro Gly Gly Ser Lys Trp Met Tyr Val Gly Arg Gln Asn<br>430 435 440 | | 1575 |
| gca gga caa aca tgg aca gat tta act ggt aat aac gga gcg tcc gtt<br>Ala Gly Gln Thr Trp Thr Asp Leu Thr Gly Asn Asn Gly Ala Ser Val<br>445 450 455 | | 1623 |
| aca att aat ggc gat gga tgg ggc gaa ttc ttt acg aat gga gga tct<br>Thr Ile Asn Gly Asp Gly Trp Gly Glu Phe Phe Thr Asn Gly Gly Ser<br>460 465 470 | | 1671 |
| gta tcc gtg tac gtg aac caa taacaaaaag ccttgagaag ggattcctcc<br>Val Ser Val Tyr Val Asn Gln<br>475 480 | | 1722 |
| ctaactcaag gctttcttta tgt | | 1745 |

<210> SEQ ID NO 27
<211> LENGTH: 501
<212> TYPE: PRT
<213> ORGANISM: Bacillus species

<400> SEQUENCE: 27

Met Arg Arg Trp Val Val Ala Met Leu Ala Val Leu Phe Leu Phe Pro
       -20              -15              -10

Ser Val Val Val Ala Asp Gly Leu Asn Gly Thr Met Met Gln Tyr Tyr
-5            -1   1                5                   10

Glu Trp His Leu Glu Asn Asp Gly Gln His Trp Asn Arg Leu His Asp
              15                  20                  25

Asp Ala Ala Ala Leu Ser Asp Ala Gly Ile Thr Ala Ile Trp Ile Pro
          30                  35                  40

-continued

```
Pro Ala Tyr Lys Gly Asn Ser Gln Ala Asp Val Gly Tyr Gly Ala Tyr
     45                  50                  55
Asp Leu Tyr Asp Leu Gly Glu Phe Asn Gln Lys Gly Thr Val Arg Thr
 60                  65                  70                  75
Lys Tyr Gly Thr Lys Ala Gln Leu Glu Arg Ala Ile Gly Ser Leu Lys
                 80                  85                  90
Ser Asn Asp Ile Asn Val Tyr Gly Asp Val Val Met Asn His Lys Met
             95                 100                 105
Gly Ala Asp Phe Thr Glu Ala Val Gln Ala Val Gln Val Asn Pro Thr
         110                 115                 120
Asn Arg Trp Gln Asp Ile Ser Gly Ala Tyr Thr Ile Asp Ala Trp Thr
     125                 130                 135
Gly Phe Asp Phe Ser Gly Arg Asn Asn Ala Tyr Ser Asp Phe Lys Trp
 140                 145                 150                 155
Arg Trp Phe His Phe Asn Gly Val Asp Trp Asp Gln Arg Tyr Gln Glu
                160                 165                 170
Asn His Ile Phe Arg Phe Ala Asn Thr Asn Trp Asn Trp Arg Val Asp
            175                 180                 185
Glu Glu Asn Gly Asn Tyr Asp Tyr Leu Leu Gly Ser Asn Ile Asp Phe
        190                 195                 200
Ser His Pro Glu Val Gln Asp Glu Leu Lys Asp Trp Gly Ser Trp Phe
    205                 210                 215
Thr Asp Glu Leu Asp Leu Asp Gly Tyr Arg Leu Asp Ala Ile Lys His
220                 225                 230                 235
Ile Pro Phe Trp Tyr Thr Ser Asp Trp Val Arg His Gln Arg Asn Glu
                240                 245                 250
Ala Asp Gln Asp Leu Phe Val Val Gly Glu Tyr Trp Lys Asp Asp Val
            255                 260                 265
Gly Ala Leu Glu Phe Tyr Leu Asp Glu Met Asn Trp Glu Met Ser Leu
        270                 275                 280
Phe Asp Val Pro Leu Asn Tyr Asn Phe Tyr Arg Ala Ser Gln Gln Gly
    285                 290                 295
Gly Ser Tyr Asp Met Arg Asn Ile Leu Arg Gly Ser Leu Val Glu Ala
300                 305                 310                 315
His Pro Met His Ala Val Thr Phe Val Asp Asn His Asp Thr Gln Pro
                320                 325                 330
Gly Glu Ser Leu Glu Ser Trp Val Ala Asp Trp Phe Lys Pro Leu Ala
            335                 340                 345
Tyr Ala Thr Ile Leu Thr Arg Glu Gly Gly Tyr Pro Asn Val Phe Tyr
        350                 355                 360
Gly Asp Tyr Tyr Gly Ile Pro Asn Asp Asn Ile Ser Ala Lys Lys Asp
    365                 370                 375
Met Ile Asp Glu Leu Leu Asp Ala Arg Gln Asn Tyr Ala Tyr Gly Thr
380                 385                 390                 395
Gln His Asp Tyr Phe Asp His Trp Asp Val Val Gly Trp Thr Arg Glu
                400                 405                 410
Gly Ser Ser Ser Arg Pro Asn Ser Gly Leu Ala Thr Ile Met Ser Asn
            415                 420                 425
Gly Pro Gly Gly Ser Lys Trp Met Tyr Val Gly Arg Gln Asn Ala Gly
        430                 435                 440
Gln Thr Trp Thr Asp Leu Thr Gly Asn Gly Ala Ser Val Thr Ile
    445                 450                 455
Asn Gly Asp Gly Trp Gly Glu Phe Phe Thr Asn Gly Gly Ser Val Ser
```

```
                460               465               470               475

Val Tyr Val Asn Gln
            480

<210> SEQ ID NO 28
<211> LENGTH: 501
<212> TYPE: PRT
<213> ORGANISM: Bacillus species

<400> SEQUENCE: 28

Met Arg Arg Trp Val Ala Met Leu Ala Val Leu Phe Leu Phe Pro
1               5                   10                  15

Ser Val Val Ala Asp Gly Leu Asn Gly Thr Met Met Gln Tyr Tyr
                20                  25                  30

Glu Trp His Leu Glu Asn Asp Gly Gln His Trp Asn Arg Leu His Asp
            35                  40                  45

Asp Ala Ala Leu Ser Asp Ala Gly Ile Thr Ala Ile Trp Ile Pro
50                  55                  60

Pro Ala Tyr Lys Gly Asn Ser Gln Ala Asp Val Gly Tyr Gly Ala Tyr
65                  70                  75                  80

Asp Leu Tyr Asp Leu Gly Glu Phe Asn Gln Lys Gly Thr Val Arg Thr
                85                  90                  95

Lys Tyr Gly Thr Lys Ala Gln Leu Glu Arg Ala Ile Gly Ser Leu Lys
            100                 105                 110

Ser Asn Asp Ile Asn Val Tyr Gly Asp Val Val Met Asn His Lys Met
        115                 120                 125

Gly Ala Asp Phe Thr Glu Ala Val Gln Ala Val Gln Val Asn Pro Thr
    130                 135                 140

Asn Arg Trp Gln Asp Ile Ser Gly Ala Tyr Thr Ile Asp Ala Trp Thr
145                 150                 155                 160

Gly Phe Asp Phe Ser Gly Arg Asn Asn Ala Tyr Ser Asp Phe Lys Trp
                165                 170                 175

Arg Trp Phe His Phe Asn Gly Val Asp Trp Asp Gln Arg Tyr Gln Glu
            180                 185                 190

Asn His Ile Phe Arg Phe Ala Asn Thr Asn Trp Asn Trp Arg Val Asp
        195                 200                 205

Glu Glu Asn Gly Asn Tyr Asp Tyr Leu Leu Gly Ser Asn Ile Asp Phe
    210                 215                 220

Ser His Pro Glu Val Gln Asp Glu Leu Lys Asp Trp Gly Ser Trp Phe
225                 230                 235                 240

Thr Asp Glu Leu Asp Leu Asp Gly Tyr Arg Leu Asp Ala Ile Lys His
                245                 250                 255

Ile Pro Phe Trp Tyr Thr Ser Asp Trp Val Arg His Gln Arg Asn Glu
            260                 265                 270

Ala Asp Gln Asp Leu Phe Val Val Gly Glu Tyr Trp Lys Asp Asp Val
        275                 280                 285

Gly Ala Leu Glu Phe Tyr Leu Asp Glu Met Asn Trp Glu Met Ser Leu
    290                 295                 300

Phe Asp Val Pro Leu Asn Tyr Asn Phe Tyr Arg Ala Ser Gln Gln Gly
305                 310                 315                 320

Gly Ser Tyr Asp Met Arg Asn Ile Leu Arg Gly Ser Leu Val Glu Ala
                325                 330                 335

His Pro Met His Ala Val Thr Phe Val Asp Asn His Asp Thr Gln Pro
            340                 345                 350
```

```
                Gly Glu Ser Leu Glu Ser Trp Val Ala Asp Trp Phe Lys Pro Leu Ala
                            355                 360                 365

Tyr Ala Thr Ile Leu Thr Arg Glu Gly Gly Tyr Pro Asn Val Phe Tyr
                        370                 375                 380

Gly Asp Tyr Tyr Gly Ile Pro Asn Asp Asn Ile Ser Ala Lys Lys Asp
                385                 390                 395                 400

Met Ile Asp Glu Leu Leu Asp Ala Arg Gln Asn Tyr Ala Tyr Gly Thr
                                405                 410                 415

Gln His Asp Tyr Phe Asp His Trp Asp Val Val Gly Trp Thr Arg Glu
                            420                 425                 430

Gly Ser Ser Ser Arg Pro Asn Ser Gly Leu Ala Thr Ile Met Ser Asn
                            435                 440                 445

Gly Pro Gly Gly Ser Lys Trp Met Tyr Val Gly Arg Gln Asn Ala Gly
                        450                 455                 460

Gln Thr Trp Thr Asp Leu Thr Gly Asn Asn Gly Ala Ser Val Thr Ile
                465                 470                 475                 480

Asn Gly Asp Gly Trp Gly Glu Phe Phe Thr Asn Gly Gly Ser Val Ser
                                485                 490                 495

Val Tyr Val Asn Gln
                            500

<210> SEQ ID NO 29
<211> LENGTH: 1920
<212> TYPE: DNA
<213> ORGANISM: Bacillus licheniformis
<220> FEATURE:
<221> NAME/KEY: CDS
<222> LOCATION: (421)..(1872)

<400> SEQUENCE: 29
cggaagattg gaagtacaaa ataagcaaa agattgtcaa tcatgtcatg agccatgcgg      60
gagacggaaa aatcgtctta atgcacgata tttatgcaac gttcgcagat gctgctgaag    120
agattattaa aaagctgaaa gcaaaaggct atcaattggt aactgtatct cagcttgaag    180
aagtgaagaa gcagagaggc tattgaataa atgagtagaa gcgccatatc ggcgcttttc    240
ttttggaaga aaatataggg aaaatggtac ttgttaaaaa ttcggaatat ttatacaaca    300
tcatatgttt cacattgaaa ggggaggaga atcatgaaac aacaaaaacg gctttacgcc    360
cgattgctga cgctgttatt tgcgctcatc ttcttgctgc tcattctgc agcagcggcg     420
```

|        |     |     |     |     |     |     |     |     |     |     |     |     |     |     |     |     |     |
|--------|-----|-----|-----|-----|-----|-----|-----|-----|-----|-----|-----|-----|-----|-----|-----|-----|-----|

```
                gca aat ctt aat ggg acg ctg atg cag tat ttt gaa tgg tac atg ccc     468
                Ala Asn Leu Asn Gly Thr Leu Met Gln Tyr Phe Glu Trp Tyr Met Pro
                1               5                   10                  15 aat gac ggc caa cat tgg agg cgt ttg caa aac gac tcg gca tat ttg     516
                Asn Asp Gly Gln His Trp Arg Arg Leu Gln Asn Asp Ser Ala Tyr Leu
                            20                  25                  30 gct gaa cac ggt att act gcc gtc tgg att ccc ccg gca tat aag gga     564
                Ala Glu His Gly Ile Thr Ala Val Trp Ile Pro Pro Ala Tyr Lys Gly
                        35                  40                  45 acg agc caa gcg gat gtg ggc tac ggt gct tac gac ctt tat gat tta     612
                Thr Ser Gln Ala Asp Val Gly Tyr Gly Ala Tyr Asp Leu Tyr Asp Leu
                    50                  55                  60 ggg gag ttt cat caa aaa ggg acg gtt cgg aca aag tac ggc aca aaa     660
                Gly Glu Phe His Gln Lys Gly Thr Val Arg Thr Lys Tyr Gly Thr Lys
                65                  70                  75                  80 gga gag ctg caa tct gcg atc aaa agt ctt cat tcc cgc gac att aac     708
                Gly Glu Leu Gln Ser Ala Ile Lys Ser Leu His Ser Arg Asp Ile Asn
                                85                  90                  95
```

```
gtt tac ggg gat gtg gtc atc aac cac aaa ggc ggc gct gat gcg acc    756
Val Tyr Gly Asp Val Val Ile Asn His Lys Gly Gly Ala Asp Ala Thr
        100                 105                 110 gaa gat gta acc gcg gtt gaa gtc gat ccc gct gac cgc aac cgc gta    804
Glu Asp Val Thr Ala Val Glu Val Asp Pro Ala Asp Arg Asn Arg Val
115                 120                 125 att tca gga gaa cac cta att aaa gcc tgg aca cat ttt cat ttt ccg    852
Ile Ser Gly Glu His Leu Ile Lys Ala Trp Thr His Phe His Phe Pro
130                 135                 140 ggg cgc ggc agc aca tac agc gat ttt aaa tgg cat tgg tac cat ttt    900
Gly Arg Gly Ser Thr Tyr Ser Asp Phe Lys Trp His Trp Tyr His Phe
145                 150                 155                 160 gac gga acc gat tgg gac gag tcc cga aag ctg aac cgc atc tat aag    948
Asp Gly Thr Asp Trp Asp Glu Ser Arg Lys Leu Asn Arg Ile Tyr Lys
            165                 170                 175 ttt caa gga aag gct tgg gat tgg gaa gtt tcc aat gaa aac ggc aac    996
Phe Gln Gly Lys Ala Trp Asp Trp Glu Val Ser Asn Glu Asn Gly Asn
        180                 185                 190 tat gat tat ttg atg tat gcc gac atc gat tat gac cat cct gat gtc    1044
Tyr Asp Tyr Leu Met Tyr Ala Asp Ile Asp Tyr Asp His Pro Asp Val
    195                 200                 205 gca gca gaa att aag aga tgg ggc act tgg tat gcc aat gaa ctg caa    1092
Ala Ala Glu Ile Lys Arg Trp Gly Thr Trp Tyr Ala Asn Glu Leu Gln
210                 215                 220 ttg gac ggt ttc cgt ctt gat gct gtc aaa cac att aaa ttt tct ttt    1140
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg    1188
Leu Arg Asp Trp Val Asn His Val Arg Glu Lys Thr Gly Lys Glu Met
            245                 250                 255 ttt acg gta gct gaa tat tgg cag aat gac ttg ggc gcg ctg gaa aac    1236
Phe Thr Val Ala Glu Tyr Trp Gln Asn Asp Leu Gly Ala Leu Glu Asn
        260                 265                 270 tat ttg aac aaa aca aat ttt aat cat tca gtg ttt gac gtg ccg ctt    1284
Tyr Leu Asn Lys Thr Asn Phe Asn His Ser Val Phe Asp Val Pro Leu
    275                 280                 285 cat tat cag ttc cat gct gca tcg aca cag gga ggc ggc tat gat atg    1332
His Tyr Gln Phe His Ala Ala Ser Thr Gln Gly Gly Gly Tyr Asp Met
290                 295                 300 agg aaa ttg ctg aac ggt acg gtc gtt tcc aag cat ccg ttg aaa tcg    1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag    1428
Val Thr Phe Val Asp Asn His Asp Thr Gln Pro Gly Gln Ser Leu Glu
            325                 330                 335 tcg act gtc caa aca tgg ttt aag ccg ctt gct tac gct ttt att ctc    1476
Ser Thr Val Gln Thr Trp Phe Lys Pro Leu Ala Tyr Ala Phe Ile Leu
        340                 345                 350 aca agg gaa tct gga tac cct cag gtt ttc tac ggg gat atg tac ggg    1524
Thr Arg Glu Ser Gly Tyr Pro Gln Val Phe Tyr Gly Asp Met Tyr Gly
    355                 360                 365 acg aaa gga gac tcc cag cgc gaa att cct gcc ttg aaa cac aaa att    1572
Thr Lys Gly Asp Ser Gln Arg Glu Ile Pro Ala Leu Lys His Lys Ile
370                 375                 380 gaa ccg atc tta aaa gcg aga aaa cag tat gcg tac gga gca cag cat    1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac    1668
Asp Tyr Phe Asp His His Asp Ile Val Gly Trp Thr Arg Glu Gly Asp
            405                 410                 415
```

```
agc tcg gtt gca aat tca ggt ttg gcg gca tta ata aca gac gga ccc      1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca      1764
Gly Gly Ala Lys Arg Met Tyr Val Gly Arg Gln Asn Ala Gly Glu Thr
    435                 440                 445 tgg cat gac att acc gga aac cgt tcg gag ccg gtt gtc atc aat tcg      1812
Trp His Asp Ile Thr Gly Asn Arg Ser Glu Pro Val Val Ile Asn Ser
450                 455                 460 gaa ggc tgg gga gag ttt cac gta aac ggc ggg tcg gtt tca att tat      1860
Glu Gly Trp Gly Glu Phe His Val Asn Gly Gly Ser Val Ser Ile Tyr
465                 470                 475                 480 gtt caa aga tag aagagcagag aggacggatt tcctgaagga aatccgtttt          1912
Val Gln Arg tttatttt                                                              1920

<210> SEQ ID NO 30
<211> LENGTH: 483
<212> TYPE: PRT
<213> ORGANISM: Bacillus licheniformis

<400> SEQUENCE: 30

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
```

-continued

```
                        260                 265                 270
Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
            290                 295             300

Arg Lys Leu Leu Asn Gly Thr Val Val Ser Lys His Pro Leu Lys Ser
305                     310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
465                 470                 475                 480

Val Gln Arg
```

ALPHA-AMYLASE MUTANTS WITH ALTERED PROPERTIES

CROSS-REFERENCE TO RELATED APPLICATIONS

This application is a continuation of U.S. application Ser. No. 12/566,238 filed Sep. 24, 2009, now abandoned, which is a continuation of U.S. application Ser. No. 10/630,203 filed Jul. 29, 2003, now abandoned, which is a continuation of U.S. application Ser. No. 09/918,543 filed Jul. 31, 2001, now abandoned, which claims the benefit or priority under 35 U.S.C. 119 of Danish Application Nos. PA 2000 01160, PA 2000 01354, PA 2000 01687 and PA 2001 00655 filed Aug. 1, 2000, Sep. 12, 2000, Nov. 10, 2000, and Apr. 26, 2001, respectively, and U.S. Provisional Application Nos. 60/225,140, 60/233,986, 60/249,104 and 60/286,869 filed on Aug. 14, 2000, Sep. 20, 2000, Nov. 16, 2000, and Apr. 26, 2001, respectively, the contents of which are fully incorporated herein by reference.

SEQUENCE LISTING

The present application contains a Sequence Listing in the form of a text file, which is incorporated herein by reference.

FIELD OF THE INVENTION

The present invention relates to variants (mutants) of parent Termamyl-like alpha-amylases, which variant has alpha-amylase activity and exhibits an alteration in at least one of the following properties relative to said parent alpha-amylase: stability under, e.g., high temperature and/or low pH conditions, in particular at low calcium concentrations. The variant of the invention are suitable for starch conversion, ethanol production, laundry wash, dish wash, hard surface cleaning, textile desizing, and/or sweetener production.

BACKGROUND OF THE INVENTION

Alpha-amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

BRIEF DISCLOSURE OF THE INVENTION

The object of the present invention is to provide Termamyl-like amylases which variants in comparison to the corresponding parent alpha-amylase, i.e., un-mutated alpha-amylase, has alpha-amylase activity and exhibits an alteration in at least one of the following properties relative to said parent alpha-amylase: stability under, e.g., high temperature and/or low pH conditions, in particular at low calcium concentrations.

Nomenclature

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)

According to this nomenclature, for instance the substitution of alanine for asparagine in position 30 is shown as:

Ala30Asn or A30N a deletion of alanine in the same position is shown as:

Ala30* or A30* and an insertion of an additional amino acid residue, such as lysine, is shown as:

Ala30AlaLys or A30AK

A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:

*36Asp or *36D for an insertion of an aspartic acid in position 36.

Multiple mutations are separated by plus signs, i.e.:

Ala30Asp+Glu34Ser or A30N+E34S representing mutations in positions 30 and 34 substituting alanine and glutamic acid for asparagine and serine, respectively.

When one or more alternative amino acid residues may be inserted in a given position it is indicated as A30N,E or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of: R,N,D,A,C,Q,E,G,H,I,L, K,M,F,P,S,T,W,Y,V.

Further, "A30X" means any one of the following substitutions:

A30R, A30N, A30D, A30C, A30Q, A30E, A30G, A30H, A30I, A30L, A30K, A30M, A30F, A30P, A30S, A30T, A30W, A30Y, or A30 V; or in short: A30R,N,D,C,Q,E,G,H, I,L,K,M,F,P,S,T,W,Y,V.

If the parent enzyme—used for the numbering—already has the amino acid residue in question suggested for substitution in that position the following nomenclature is used:

"X30N" or "X30N,V"

in the case where for instance one or N or V is present in the wildtype.

Thus, it means that other corresponding parent enzymes are substituted to an "Asn" or "Val" in position 30.

BRIEF DESCRIPTION OF THE DRAWINGS

FIG. 1 is an alignment of the amino acid sequences of five parent Termamyl-like alpha-amylases. The numbers on the extreme left designate the respective amino acid sequences as follows:

1: SEQ ID NO: 4 (SP722)

2: SEQ ID NO: 2 (SP690)

3: SEQ ID NO: 10 (BAN)

4: SEQ ID NO: 8 (BLA)

5: SEQ ID NO: 6 (BSG).

DETAILED DISCLOSURE OF THE INVENTION

The object of the present invention is to provide Termamyl-like amylases, which variants have alpha-amylase activity and exhibits altered stability at high temperatures and/or at low pH, in particular at low calcium concentrations.

Termamyl-Like Alpha-Amylases

A number of alpha-amylases produced by *Bacillus* spp. are highly homologous (identical) on the amino acid level.

The identity of a number of known *Bacillus* alpha-amylases can be found in the below Table 1:

TABLE 1

| Percent identity | 707 | AP1378 | BAN | BSG | SP690 | SP722 | AA560 | Termamyl |
|---|---|---|---|---|---|---|---|---|
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| Termamyl | 68.1 | 69.4 | 80.7 | 65.4 | 69.2 | 70.8 | 68.3 | 100.0 |

For instance, the *B. licheniformis* alpha-amylase comprising the amino acid sequence shown in SEQ ID NO: 8 (commercially available as Termamyl™) has been found to be about 81% homologous with the *B. amyloliquefaciens* alpha-amylase comprising the amino acid sequence shown in SEQ ID NO: 10 and about 65% homologous with the *B. stearothermophilus* alpha-amylase (BSG) comprising the amino acid sequence shown in SEQ ID NO: 6. Further homologous alpha-amylases include SP690 and SP722 disclosed in WO 95/26397 and further depicted in SEQ ID NO: 2 and SEQ ID NO: 4, respectively, herein. Other amylases are the AA560 alpha-amylase derived from *Bacillus* sp. and shown in SEQ ID NO: 12, and the #707 alpha-amylase derived from *Bacillus* sp., shown in SEQ ID NO: 13 and described by Tsukamoto et al., 1988, *Biochemical and Biophysical Research Communications* 151: 25-31.

The KSM AP1378 alpha-amylase is disclosed in WO 97/00324 (from KAO Corporation).

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: Optitherm™ and Takatherm™ (Solvay); Maxamyl™ (available from Gist-brocades/Genencor), Spezym AA™ and Spezyme Delta AA™ (available from Genencor), and Keistase™ (available from Daiwa), Dex lo, GC 521 (available from Genencor) and Ultraphlow (from Enzyme Biosystems).

Because of the substantial homology found between these alpha-amylases, they are considered to belong to the same class of alpha-amylases, namely the class of "Termamyl-like alpha-amylases".

Accordingly, in the present context, the term "Termamyl-like" alpha-amylase" is intended to indicate an alpha-amylase, in particular *Bacillus* alpha-amylase, which, at the amino acid level, exhibits a substantial identity to Termamyl™, i.e., the *B. licheniformis* alpha-amylase having the amino acid sequence shown in SEQ ID NO: 8, herein.

In other words, all of the following alpha-amylases, which have the amino acid sequences shown in SEQ ID NOS: 2, 4, 6, 8, 10, 12 and 13 herein, are considered to be "Termamyl-like alpha-amylase". Other Termamyl-like alpha-amylases are alpha-amylases i) which display at least 60%, such as at least 70%, e.g., at least 75%, or at least 80%, at least 85%, at least 90%, at least 95%, at least 97%, at least 99% homology (identity) with at least one of said amino acid sequences shown in SEQ ID NOS: 2, 4, 6, 8, 10, 12, and 13, and/or are encoded by a DNA sequence which hybridizes to the DNA sequences encoding the above-specified alpha-amylases which are apparent from SEQ ID NOS: 1, 3, 5, 7, 9, and of the present specification (which encoding sequences encode the amino acid sequences shown in SEQ ID NOS: 2, 4, 6, 8, 10 and 12 herein, respectively).

Homology

The homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, 1970, *J. Mol. Biol.* 48: 443-453, to make alignments and to calculate the identity.

A structural alignment between Termamyl (SEQ ID NO: 8) and, e.g., another alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., 1987, *FEBS Letters* 224: 149-155) and reverse threading (Huber and Torda, 1998, *Protein Science* 7(1): 142-149).

Hybridization

The oligonucleotide probe used in the characterization of the Termamyl-like alpha-amylase above may suitably be prepared on the basis of the full or partial nucleotide or amino acid sequence of the alpha-amylase in question.

Suitable conditions for testing hybridization involve presoaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferably at 50° C. (medium stringency), more preferably at 65° C. (high stringency), even more preferably at 75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Parent Termamyl-Like Alpha-Amylases

According to the invention all Termamy-like alpha-amylases, as defined above, may be used as the parent (i.e., backbone) alpha-amylase. In a preferred embodiment of the invention the parent alpha-amylase is derived from *B. licheniformis*, e.g., one of those referred to above, such as the *B. licheniformis* alpha-amylase having the amino acid sequence shown in SEQ ID NO: 8.

Parent Hybrid Termamyl-Like Alpha-Amylases

The parent alpha-amylase (i.e., backbone alpha-amylase) may also be a hybrid alpha-amylase, i.e., an alpha-amylase, which comprises a combination of partial amino acid sequences derived from at least two alpha-amylases.

The parent hybrid alpha-amylase may be one, which on the basis of amino acid homology (identity) and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives, may be any of the specific Termamyl-like alpha-amylase referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus*. For instance, the parent alpha-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 10 and an amino acid segment corresponding to the 445 C-terminal amino acid residues of the *B. licheniformis* alpha-amylase having the amino acid sequence shown in SEQ ID NO: 8, or a hybrid Termamyl-like alpha-amylase being identical to the Termamyl sequence, i.e., the *Bacillus licheniformis* alpha-amylase shown in SEQ ID NO: 8, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 10; or b) an amino acid segment corresponding to the 68 N-terminal amino acid residues of the *B. stearothermophilus* alpha-amylase having the amino acid sequence shown in SEQ ID NO: 6 and an amino acid segment corresponding to the 415 C-terminal amino acid residues of the *B. licheniformis* alpha-amylase having the amino acid sequence shown in SEQ ID NO: 8.

Another suitable parent hybrid alpha-amylase is the one previously described in WO 96/23874 (from Novo Nordisk) constituting the N-terminus of BAN, *Bacillus amyloliquefaciens* alpha-amylase (amino acids 1-300 of the mature protein) and the C-terminus from Termamyl (amino acids 301-483 of the mature protein).

In a preferred embodiment of the invention the parent Termamyl-like alpha-amylase is a hybrid alpha-amylase of SEQ ID NO: 8 and SEQ ID NO: 10. Specifically, the parent hybrid Termamyl-like alpha-amylase may be a hybrid alpha-amylase comprising the 445 C-terminal amino acid residues of the *B. licheniformis* alpha-amylase shown in SEQ ID NO: 8 and the 37 N-terminal amino acid residues of the alpha-amylase derived from *B. amyloliquefaciens* shown in SEQ ID NO: 10, which may suitably further have the following mutations: H156Y+A181T+N190F+A209V+Q264S (using the numbering in SEQ ID NO: 8). The latter mentioned hybrid is used in the examples below and is referred to as LE174.

Other specifically contemplated parent alpha-amylase include LE174 with fewer mutations, i.e., the right above mentioned hydrid having the following mutations: A181T+N190F+A209V+Q264S; N190F+A209V+Q264S; A209V+Q264S; Q264S; H156Y+N190F+A209V+Q264S; H156Y+A209V+Q264S; H156Y+Q264S; H156Y+A181T+A209V+Q264S; H156Y+A181T+Q264S; H156Y+Q264S; H156Y+A181T+N190F+Q264S; H156Y+A181T+N190F; H156Y+A181T+N190F+A209V. These hybrids are also considered to be part of the invention.

In a preferred embodiment the parent Termamyl-like alpha amylase is LE174, SP722, or AA560 including any of

LE174+G48A+T49I+G107A+I201F;

LE174+M197L;

LE174+G48A+T49I+G107A+M197L+I201F;

SP722+D183*+G184*;

SP722+D183*+G184*+N195F;

SP722+D183*+G184*+M202L;

SP722+D183*+G184*+N195F+M202L;

BSG+I181*+G182*;

BSG+I181*+G182*+N193F;

BSG+I181*+G182*+M200L;

BSG+I181*+G182*+N193F+M200L;

AA560+D183*+G184*;

AA560+D183*+G184*+N195F; AA560+D183*+G184*+M202L;

AA560+D183*+G184*+N195F+M202L.

Other parent alpha-amylases contemplated include LE429, which is LE174 with an additional substitution in I201F. According to the invention LE335 is the alpha-amylase, which in comparison to LE429 has additional substitutions in T49I+G107A; LE399 is LE335+G48A, i.e., LE174, with G48A+T49I+G107A+I201F.

Altered Properties

The following section discusses the relationship between mutations, which are present in variants of the invention, and desirable alterations in properties (relative to those of a parent Termamyl-like alpha-amylase), which may result therefrom.

As mentioned above the invention relates to Termamyl-like alpha-amylases with altered properties (as mentioned above), in particular at high temperatures and/or at low pH, in particular at low calcium concentrations.

In the context of the present invention "high temperature" means temperatures from 70-120° C., preferably 80-100° C., especially 85-95° C.

In the context of the present invention the term "low pH" means from a pH in the range from 4-6, preferably 4.2-5.5, especially 4.5-5.

In the context of the present invention the term "high pH" means from a pH in the range from 8-11, especially 8.5-10.6.

In the context of the present invention the term "low calcium concentration" means free calcium levels lower than 60 ppm, preferably 40 ppm, more preferably 25 ppm, especially 5 ppm calcium.

Parent Termamyl-like alpha-amylase specifically contemplated in connection with going through the specifically contemplated altered properties are the above mentioned parent Termamyl-like alpha-amylase and parent hydrid Termamyl-like alpha-amylases.

The Termamyl® alpha-amylase is used as the starting point, but corresponding positions in, e.g., the SP722, BSG, BAN, AA560, SP690, KSM AP1378, and #707 should be understood as disclosed and specifically contemplated too.

In a preferred embodiment the variant of the invention has in particular at high temperatures and/or at low pH.

In an aspect the invention relates to variant with altered properties as mentioned above.

In the first aspect a variant of a parent Termamyl-like alpha-amylase, comprising an alteration at one or more positions (using SEQ ID NO: 8 for the amino acid numbering) selected from the group of:

49, 60, 104, 132, 161, 170, 176, 179, 180, 181, 183, 200, 203, 204, 207, 212, 237, 239, 250, 280, 298, 318, 374, 385, 393, 402, 406, 427, 430, 440, 444, 447, 482, wherein (a) the alteration(s) are independently
  (i) an insertion of an amino acid downstream of the amino acid which occupies the position,
  (ii) a deletion of the amino acid which occupies the position, or
  (iii) a substitution of the amino acid which occupies the position with a different amino acid, (b) the variant has alpha-amylase activity and (c) each position corresponds to a position of the amino acid sequence of the parent Termamyl-like alpha-amylase having the amino acid sequence shown in SEQ ID NO: 8.

In Termamyl® (SEQ ID NO: 8) such corresponding positions are:

T49; D60; N104; E132; D161; K170; K176; G179; K180; A181; D183; D200; Y203; D204; D207; 1212; K237; S239; E250; N280; Q298; L318; Q374; E385; Q393; Y402; H406; L427; D430; V440; N444; E447; Q482.

In SP722 (SEQ ID NO: 4) the corresponding positions are:

T51; D62; N106; D134; D163; Q172; K179; G184; K185; A186; D188; D205; M208; D209; X212; L217; K242, S244, N255, N285, S303, M323; D387, N395; Y404; H408; 1429; D432; V442; K446; Q449; K484.

Corresponding positions in other parent alpha-amylases can be found by alignment as described above and shown in the alignment in FIG. 1.

In a preferred embodiment the variant of the invention (using SEQ ID NO: 8 (Termamyl™) for the numbering) has one or more of the following substitutions:

T49I; D60N; N104D; E132A,V,P; D161N; K170Q; K176R; G179N; K180T; A181N; D183N; D200N; X203Y; D204S; D207V,E,L,G; X212I; K237P; S239W; E250G,F; N280S; X298Q; L318M; Q374R; E385V; Q393R; Y402F; H406L,W; L427I; D430N; V440A; N444R,K; E447Q,K; Q482K.

In a preferred embodiment the variant of the invention (using SEQ ID NO: 4 (SP722) for the numbering) has one or more of the following substitutions:

T51I; D62N; N106D; D134A,V,P; D163N; X172Q; K179R; G184N; K185T; A186N; D188N; D205N; M208Y; D209S; X212V,E,L,G; L217I, K242P, S244W, N255G,F, N285S, S303Q, X323M; D387V, N395R; Y404F; H408L,W; X429I; D432N; V442A; X446R,K; X449Q,K; X484K, using SEQ ID NO: 4 (SP722) for numbering.

Preferred double, triple and multi-mutations—using SEQ ID NO: 8 as the basis for the numbering are selected from the group consisting of:

T49I+D60N; T49I+D60N+E132A; T49I+D60N+E132V; T49I+D60N+E132V+K170Q;

T49I+D60N+E132A+K170Q; T49I+D60N+E132V+K170Q+K176R;

T49I+D60N+E132A+K170Q+K176R;

T49I+D60N+E132V+K170Q+K176R+D207V; T49I+D60N+E132A+K170Q+K176R+D207V;

T49I+D60N+E132V+K170Q+K176R+D207E; T49I+D60N+E132A+K170Q+K176R+D207E;

T49I+D60N+E132V+K170Q+K176R+D207V+E250G;

T49I+D60N+E132A+K170Q+K176R+D207V+E250G;

T49I+D60N+E132V+K170Q+K176R+D207E+E250G;

T49I+D60N+E132A+K170Q+K176R+D207E+E250G;

T49I+D60N+E132V+K170Q+K176R+D207E+E250G+N280S;

T49I+D60N+E132A+K170Q+K176R+D207E+E250G+N280S;

T49I+D60N+E132V+K170Q+K176R+D207V+E250G+N280S;

T49I+D60N+E132A+K170Q+K176R+D207V+E250G+N280S;

T49I+D60N+E132V+K170Q+K176R+D207V+E250G+N280S+L318M;

T49I+D60N+E132A+K170Q+K176R+D207V+E250G+N280S+L318M;

T49I+D60N+E132V+K170Q+K176R+D207E+E250G+N280S+L318M;

T49I+D60N+E132A+K170Q+K176R+D207E+E250G+N280S+L318M;

T49I+D60N+E132V+K170Q+K176R+D207V+E250G+N280S+L318M+Q374R;

T49I+D60N+E132A+K170Q+K176R+D207V+E250G+
N280S+L318M+Q374R;

T49I+D60N+E132V+K170Q+K176R+D207E+E250G+
N280S+L318M+Q374R;

T49I+D60N+E132A+K170Q+K176R+D207E+E250G+
N280S+L318M+Q374R;

T49I+D60N+E132V+K170Q+K176R+D207V+E250G+
N280S+L318M+Q374R+E385V;

T49I+D60N+E132A+K170Q+K176R+D207V+E250G+
N280S+L318M+Q374R+E385V;

T49I+D60N+E132V+K170Q+K176R+D207E+E250G+
N280S+L318M+Q374R+E385V;

T49I+D60N+E132A+K170Q+K176R+D207E+E250G+
N280S+L318M+Q374R+E385V;

T49I+D60N+E132V+K170Q+K176R+D207V+E250G+
N280S+L318M+Q374R+E385V+Q393R;

T49I+D60N+E132A+K170Q+K176R+D207V+E250G+
N280S+L318M+Q374R+E385V+Q393R;

T49I+D60N+E132V+K170Q+K176R+D207E+E250G+
N280S+L318M+Q374R+E385V+Q393R;

T49I+D60N+E132A+K170Q+K176R+D207E+E250G+
N280S+L318M+Q374R+E385V+Q393R;

T49I+D60N+E132V+K170Q+K176R+D207V+E250G+
N280S+L318M+Q374R+E385V+Q393R+Y402F;

T49I+D60N+E132A+K170Q+K176R+D207V+E250G+
N280S+L318M+Q374R+E385V+Q393R+Y402F;

T49I+D60N+E132V+K170Q+K176R+D207E+E250G+
N280S+L318M+Q374R+E385V+Q393R+Y402F;

T49I+D60N+E132A+K170Q+K176R+D207E+E250G+
N280S+L318M+Q374R+E385V+Q393R+Y402F;

T49I+D60N+E132V+K170Q+K176R+D207V+E250G+
N280S+L318M+Q374R+E385V+Q393R+Y402F+H406L;

T49I+D60N+E132A+K170Q+K176R+D207V+E250G+
N280S+L318M+Q374R+E385V+Q393R+Y402F+H406L;

T49I+D60N+E132V+K170Q+K176R+D207E+E250G+
N280S+L318M+Q374R+E385V+Q393R+Y402F+H406L;

T49I+D60N+E132A+K170Q+K176R+D207E+E250G+
N280S+L318M+Q374R+E385V+Q393R+Y402F+H406L;

T49I+D60N+E132V+K170Q+K176R+D207V+E250G+
N280S+L318M+Q374R+E385V+Q393R+Y402F+H406L+
L427I;

T49I+D60N+E132A+K170Q+K176R+D207V+E250G+
N280S+L318M+Q374R+E385V+Q393R+Y402F+H406L+
L427I;

T49I+D60N+E132V+K170Q+K176R+D207E+E250G+
N280S+L318M+Q374R+E385V+Q393R+Y402F+H406L+
L427I;

T49I+D60N+E132A+K170Q+K176R+D207E+E250G+
N280S+L318M+Q374R+E385V+Q393R+Y402F+H406L+
L427I;

T49I+D60N+E132V+K170Q+K176R+D207V+E250G+
N280S+L318M+Q374R+E385V+Q393R+Y402F+H406L+
L427I+V440A;

T49I+D60N+E132A+K170Q+K176R+D207V+E250G+
N280S+L318M+Q374R+E385V+Q393R+Y402F+H406L+
L427I+V440A;

T49I+D60N+E132V+K170Q+K176R+D207E+E250G+
N280S+L318M+Q374R+E385V+Q393R+Y402F+H406L+
L427I+V440A;

T49I+D60N+E132A+K170Q+K176R+D207E+E250G+
N280S+L318M+Q374R+E385V+Q393R+Y402F+H406L+
L427I+V440A;

D60N+E132A; D60N+E132V; D60N+E132V+K170Q;
D60N+E132A+K170Q;

D60N+E132V+K170Q+K176R; T49I+D60N+E132A+
K170Q+K176R;

D60N+E132V+K170Q+K176R+D207V; T49I+D60N+
E132A+K170Q+K176R+D207V;

D60N+E132V+K170Q+K176R+D207E; T49I+D60N+
E132A+K170Q+K176R+D207E;

D60N+E132V+K170Q+K176R+D207V+E250G;

D60N+E132A+K170Q+K176R+D207V+E250G;

D60N+E132V+K170Q+K176R+D207E+E250G;

D60N+E132A+K170Q+K176R+D207E+E250G;

D60N+E132V+K170Q+K176R+D207V+E250G+N280S;

D60N+E132A+K170Q+K176R+D207V+E250G+N280S;

D60N+E132V+K170Q+K176R+D207E+E250G+N280S;

D60N+E132A+K170Q+K176R+D207E+E250G+N280S;

D60N+E132V+K170Q+K176R+D207V+E250G+N280S+
L318M;

D60N+E132A+K170Q+K176R+D207V+E250G+N280S+
L318M;

D60N+E132V+K170Q+K176R+D207E+E250G+N280S+
L318M;

D60N+E132A+K170Q+K176R+D207E+E250G+N280S+
L318M;

D60N+E132V+K170Q+K176R+D207V+E250G+N280S+
L318M+Q374R;

D60N+E132A+K170Q+K176R+D207V+E250G+N280S+
L318M+Q374R;

D60N+E132V+K170Q+K176R+D207E+E250G+N280S+
L318M+Q374R;

D60N+E132A+K170Q+K176R+D207E+E250G+N280S+
L318M+Q374R;

D60N+E132V+K170Q+K176R+D207V+E250G+N280S+
L318M+Q374R+E385V;

D60N+E132A+K170Q+K176R+D207V+E250G+N280S+
L318M+Q374R+E385V;

D60N+E132V+K170Q+K176R+D207E+E250G+N280S+
L318M+Q374R+E385V;

D60N+E132A+K170Q+K176R+D207E+E250G+N280S+
L318M+Q374R+E385V;

D60N+E132V+K170Q+K176R+D207V+E250G+N280S+
L318M+Q374R+E385V+Q393R+Y402F;

D60N+E132A+K170Q+K176R+D207V+E250G+N280S+
L318M+Q374R+E385V+Q393R+Y402F;

D60N+E132V+K170Q+K176R+D207E+E250G+N280S+ L318M+Q374R+E385V+Q393R+Y402F;

D60N+E132A+K170Q+K176R+D207E+E250G+N280S+ L318M+Q374R+E385V+Q393R+Y402F;

D60N+E132V+K170Q+K176R+D207V+E250G+N280S+ L318M+Q374R+E385V+Q393R+Y402F+H406L;

D60N+E132A+K170Q+K176R+D207V+E250G+N280S+ L318M+Q374R+E385V+Q393R+Y402F+H406L;

D60N+E132V+K170Q+K176R+D207E+E250G+N280S+ L318M+Q374R+E385V+Q393R+Y402F+H406L;

D60N+E132A+K170Q+K176R+D207E+E250G+N280S+ L318M+Q374R+E385V+Q393R+Y402F+H406L;

D60N+E132V+K170Q+K176R+D207V+E250G+N280S+ L318M+Q374R+E385V+Q393R+Y402F+H406L+L427I;

D60N+E132A+K170Q+K176R+D207V+E250G+N280S+ L318M+Q374R+E385V+Q393R+Y402F+H406L+L427I;

D60N+E132V+K170Q+K176R+D207E+E250G+N280S+ L318M+Q374R+E385V+Q393R+Y402F+H406L+L427I;

D60N+E132A+K170Q+K176R+D207E+E250G+N280S+ L318M+Q374R+E385V+Q393R+Y402F+H406L+L427I;

D60N+E132V+K170Q+K176R+D207V+E250G+N280S+ L318M+Q374R+E385V+Q393R+Y402F+H406L+L427I+ V440A;

D60N+E132A+K170Q+K176R+D207V+E250G+N280S+ L318M+Q374R+E385V+Q393R+Y402F+H406L+L427I+ V440A;

D60N+E132V+K170Q+K176R+D207E+E250G+N280S+ L318M+Q374R+E385V+Q393R+Y402F+H406L+L427I+ V440A;

D60N+E132A+K170Q+K176R+D207E+E250G+N280S+ L318M+Q374R+E385V+Q393R+Y402F+H406L+L427I+ V440A;

E132V+K170Q; E132A+K170Q; E132V+K170Q+K176R; E132A+K170Q+K176R;

E132V+K170Q+K176R+D207V; E132A+K170Q+K176R+ D207V;

E132V+K170Q+K176R+D207E; E132A+K170Q+K176R+ D207E;

E132V+K170Q+K176R+D207V+E250G; E132A+K170Q+ K176R+D207V+E250G;

E132V+K170Q+K176R+D207E+E250G; E132A+K170Q+ K176R+D207E+E250G;

E132V+K170Q+K176R+D207E+E250G+N280S;

E132A+K170Q+K176R+D207E+E250G+N280S;

E132V+K170Q+K176R+D207V+E250G+N280S;

E132A+K170Q+K176R+D207V+E250G+N280S;

E132V+K170Q+K176R+D207V+E250G+N280S+L318M;

E132A+K170Q+K176R+D207V+E250G+N280S+L318M;

E132V+K170

E132A+K170Q+K176R+D207E+E250G+N280S+L318M+
Q374R+E385V+Q393R+Y402F+H406L+L427I+V440A;

K170Q+K176R; K170Q+K176R+D207V; K170Q+K176R+
D207E;

K170Q+K176R+D207V+E250G; K170Q+K176R+D207E+
E250G;

K170Q+K176R+D207V+E250G+N280S; K170Q+K176R+
D207E+E250G+N280S;

K170Q+K176R+D207E+E250G+N280S+L318M;

K170Q+K176R+D207V+E250G+N280S+L318M;

K170Q+K176R+D207E+E250G+N280S+L318M+Q374R;

K170Q+K176R+D207V+E250G+N280S+L318M+Q374R;

K170Q+K176R+D207E+E250G+N280S+L318M+
Q374R+E385V;

K170Q+K176R+D207V+E250G+N280S+L318M+
Q374R+E385V;

K170Q+K176R+D207V+E250G+N280S+L318M+
Q374R+E385V+Q393R;

K170Q+K176R+D207E+E250G+N280S+L318M+
Q374R+E385V+Q393R;

K170Q+K176R+D207V+E250G+N280S+L318M+
Q374R+E385V+Q393R+Y402F;

K170Q+K176R+D207E+E250G+N280S+L318M+
Q374R+E385V+Q393R+Y402F;

K170Q+K176R+D207V+E250G+N280S+L318M+
Q374R+E385V+Q393R+Y402F+H406L;

K170Q+K176R+D207E+E250G+N280S+L318M+
Q374R+E385V+Q393R+Y402F+H406L;

K170Q+K176R+D207V+E250G+N280S+L318M+
Q374R+E385V+Q393R+Y402F+H406L+L427I;

K170Q+K176R+D207E+E250G+N280S+L318M+
Q374R+E385V+Q393R+Y402F+H406L+L427I;

K170Q+K176R+D207V+E250G+N280S+L318M+
Q374R+E385V+Q393R+Y402F+H406L+L427I+V440A;

K170Q+K176R+D207E+E250G+N280S+L318M+
Q374R+E385V+Q393R+Y402F+H406L+L427I+V440A;

K176R+D207V; K176R+D207E; K176R+D207V+E250G;

K176R+D207E+E250G; K176R+D207V+E250G+N280S;

K176R+D207E+E250G+N280S; K176R+D207E+E250G+
N280S+L318M;

K176R+D207V+E250G+N280S+L318M;

K176R+D207E+E250G+N280S+L318M+Q374R;

K176R+D207V+E250G+N280S+L318M+Q374R;

K176R+D207E+E250G+N280S+L318M+Q374R+E385V;

K176R+D207V+E250G+N280S+L318M+Q374R+E385V;

K176R+D207V+E250G+N280S+L318M+Q374R+
E385V+Q393R;

K176R+D207E+E250G+N280S+L318M+Q374R+E385V+
Q393R;

K176R+D207V+E250G+N280S+L318M+Q374R+
E385V+Q393R+Y402F;

K176R+D207E+E250G+N280S+L318M+Q374R+E385V+
Q393R+Y402F;

K176R+D207V+E250G+N280S+L318M+Q374R+
E385V+Q393R+Y402F+H406L;

K176R+D207V+E250G+N280S+L318M+Q374R+
E385V+Q393R+Y402F+H406L+L427I;

K176R+D207E+E250G+N280S+L318M+Q374R+E385V+
Q393R+Y402F+H406L+L427I;

K176R+D207V+E250G+N280S+L318M+Q374R+
E385V+Q393R+Y402F+H406L+L427I+V440A;

K176R+D207E+E250G+N280S+L318M+Q374R+E385V+
Q393R+Y402F+H406L+L427I+V440A;

D207V+E250G; D207E+E250G;

D207V+E250G+N280S; D207E+E250G+N280S+L318M;

D207V+E250G+N280S+L318M; D207E+E250G+N280S+
L318M+Q374R;

D207V+E250G+N280S+L318M+Q374R;

D207E+E250G+N280S+L318M+Q374R+E385V;

D207V+E250G+N280S+L318M+Q374R+E385V;

D207V+E250G+N280S+L318M+Q374R+E385V+Q393R;

D207E+E250G+N280S+L318M+Q374R+E385V+Q393R;

D207V+E250G+N280S+L318M+Q374R+E385V+
Q393R+Y402F;

D207E+E250G+N280S+L318M+Q374R+E385V+Q393R+
Y402F;

D207V+E250G+N280S+L318M+Q374R+E385V+
Q393R+Y402F+H406L;

D207E+E250G+N280S+L318M+Q374R+E385V+Q393R+
Y402F+H406L;

D207V+E250G+N280S+L318M+Q374R+E385V+
Q393R+Y402F+H406L+L427I;

D207E+E250G+N280S+L318M+Q374R+E385V+Q393R+
Y402F+H406L+L427I;

D207V+E250G+N280S+L318M+Q374R+E385V+
Q393R+Y402F+H406L+L427I+V440A;

D207E+E250G+N280S+L318M+Q374R+E385V+Q393R+
Y402F+H406L+L427I+V440A;

E250G+N280S; E250G+N280S+L318M; E250G+N280S+
L318M+Q374R;

E250G+N280S+L318M+Q374R+E385V;

E250G+N280S+L318M+Q374R+E385V+Q393R;

E250G+N280S+L318M+Q374R+E385V+Q393R+Y402F;

E250G+N280S+L318M+Q374R+E385V+Q393R+Y402F+
H406L;

E250G+N280S+L318M+Q374R+E385V+Q393R+Y402F+
H406L+L427I;

E250G+N280S+L318M+Q374R+E385V+Q393R+Y402F+
H406L+L427I+V440A;

N280S+L318M; N280S+L318M+Q374R; N280S+L318M+
Q374R+E385V;

N280S+L318M+Q374R+E385V+Q393R;

N280S+L318M+Q374R+E385V+Q393R+Y402F;

N280S+L318M+Q374R+E385V+Q393R+Y402F+H406L;

N280S+L318M+Q374R+E385V+Q393R+Y402F+H406L+ L427I;

N280S+L318M+Q374R+E385V+Q393R+Y402F+H406L+ L427I+V440A;

L318M+Q374R; L318M+Q374R+E385V; L318M+ Q374R+E385V+Q393R;

L318M+Q374R+E385V+Q393R+Y402F;

L318M+Q374R+E385V+Q393R+Y402F+H406L;

L318M+Q374R+E385V+Q393R+Y402F+H406L+L427I;

L318M+Q374R+E385V+Q393R+Y402F+H406L+L427I+ V440A;

Q374R+E385V; Q374R+E385V+Q393R; Q374R+E385V+ Q393R+Y402F;

Q374R+E385V+Q393R+Y402F+H406L;

Q374R+E385V+Q393R+Y402F+H406L+L427I;

Q374R+E385V+Q393R+Y402F+H406L+L427I+V440A;

E385V+Q393R; E385V+Q393R+Y402F; E385V+Q393R+ Y402F+H406L;

E385V+Q393R+Y402F+H406L+L427I;

E385V+Q393R+Y402F+H406L+L427I+V440A;

Q393R+Y402F; Q393R+Y402F+H406L; Q393R+Y402F+ H406L+L427I;

Q393R+Y402F+H406L+L427I+V440A; Y402F+H406L;

Y402F+H406L+L427I; Y402F+H406L+L427I+V440A; H406L+L427I;

H406L+L427I+V440A; L427I+V440A;

N104D+D161N+G179N+K180T+A181N+D183N+ D200N+D204S+K237P+S239W+H406W+D430N+ N444K+E447Q+Q482K;

D161N+G179N+K180T+A181N+D183N+D200N+ D204S+K237P+S239W+H406W+D430N+N444K+ E447Q+Q482K;

D161N+A181N+D183N+D200N+D204S+K237P+ S239W+H406W+D430N+N444K+E447Q+Q482K;

D161N+A181N+D183N+D200N+D204S+K237P+ S239W+H406W+D430N+E447Q+Q482K;

N104D+D161N+G179N+K180T+A181N+D183N+ D200N+D204S+K237P+S239W+H406W+D430N+ E447Q+Q482K;

D161N+G179N+K180T+A181N+D183N+D200N+ D204S+K237P+S239W+H406W+D430N+E447Q+ Q482K;

N104D+D161N+G179N+K180T+A181N+D183N+ D200N+D204S+K237P+S239W+H406W+D430N;

D161N+G179N+K180T+A181N+D183N+D200N+ D204S+K237P+S239W+H406W+D430N;

H406W+D430N; N444K+E447Q+Q482K; E447Q+Q482K;

N104D+D161N+G179N+K180T+A181N+D183N+ D200N+D204S+K237P+S239W+H406W+ D430N+N444R+N444K+E447K+Q482K;

D161N+G179N+K180T+A181N+D183N+D200N+ D204S+K237P+S239W+H406W+D430N+N444R+ N444K+E447K+Q482K;

N104D+D161N+G179N+K180T+A181N+D183N+ D200N+D204S+K237P+S239W;

D161N+G179N+K180T+A181N+D183N+D200N+ D204S+K237P+S239W;

H406W+D430N; N444K+E447K+Q482K; E447K+Q482K;

N104D+D161N+A181N+D183N+D200N+D204S+ K237P+S239W;

N104D+D161N+A181N+D183N+D200N+D204S+K237P;

N104D+D161N+A181N+D183N+D200N+D204S;

D161N+A181N+D183N+D200N+D204S+K237P+S239W;

D161N+A181N+D183N+D200N+D204S+K237P;

D161N+A181N+D183N+D200N+D204S; K237P+S239W, using SEQ ID NO: 8 for numbering.

In a preferred embodiment the variant has the following substitutions: K170Q+D207V+N280S; E132A+D207V; D207E+E250G+H406L+L427I; D207V+L318M; D60N+ D207V+L318M; T491+E132V+V440A; T49I+K176R+ D207V+Y402F; Q374R+E385V+Q393R; N190F+A209V+ Q264S; G48A+T49I+G107A+I201F; T49I+G107A+I201F; G48A+T49I+I201F; G48A+T49I+G107A; T491+I201F; T49I+G107A; G48A+T49I; D161N+G179N+K180T+ A181N+D183N+D200N+D204S+K237P+S239W+ H406W+D430N+N444R+E447Q+Q482K using SEQ ID NO: 8 for numbering.

Specific variants include: LE399; LE174+G48A+T49I+ G107A; LE174+G48A+T49I+I201F; LE174+G48A+ G107A+I201F; LE174+T49I+G107A+I201F; LE174+ G48A+T49I; LE174+G48A; LE174+G107A+I201F; and LE174+I201F.

Stability

In the context of the present invention, mutations (including amino acid substitutions and deletions) of importance with respect to achieving altered stability, in particular improved stability (i.e., higher or lower), at especially high temperatures (i.e., 70-120° C.) and/or extreme pH (i.e., low or high pH, i.e., pH 4-6 or pH 8-11, respectively), in particular at free (i.e., unbound, therefore in solution) calcium concentrations below 60 ppm, include any of the mutations listed in the "Altered properties" section. The stability may be determined as described in the "Materials & Methods" section below.

General Mutations in Variants of the Invention

A variant of the invention may in one embodiment comprise one or more modifications in addition to those outlined above. Thus, it may be advantageous that one or more Proline (Pro) residues present in the part of the alpha-amylase variant which is modified is/are replaced with a non-Proline residue which may be any of the possible, naturally occurring non-Proline residues, and which preferably is an Alanine, Glycine, Serine, Threonine, Valine or Leucine.

Analogously, in one embodiment one or more Cysteine residues present in the parent alpha-amylase may be replaced with a non-Cysteine residue such as Serine, Alanine, Threonine, Glycine, Valine or Leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 10 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 10 by an Arg.

It is to be understood that the present invention encompasses variants incorporating two or more of the above outlined modifications.

Furthermore, it may be advantageous to introduce mutations in one or more of the following positions (using SEQ ID NO: 8 (Termamyl) for numbering):

M15, V128, A111, H133, W138, T149, M197, N188, A209, A210, H405, T412, in particular the following single, double or triple or multi mutations:

M15X, in particular M15T,L;

V128X, in particular V128E;

H133X, in particular H133Y;

N188X, in particular N188S,T,P;

M197X, in particular M197T,L;

A209X, in particular A209V;

M197T/W138F; M197T/W138Y; M15T/H133Y/N188S;

M15/V128E/H133Y/N188S; E119C/S130C; D124C/R127c; H133Y/T149I;

G475R, H133Y/S187D; H133Y/A209V.

Methods for Preparing Alpha-Amylase Variants of the Invention

Several methods for introducing mutations into genes are known in the art. After a brief description of cloning of alpha-amylase-encoding DNA sequences, methods for generating mutations at specific sites within the alpha-amylase-encoding sequence will be described.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by Beaucage and Caruthers, 1981, *Tetrahedron Letters* 22: 1859-1869, or the method described by Matthes et al., 1984, *The EMBO J.* 3: 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al., 1988, *Science* 239: 487-491.

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants of the invention include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question. Examples of parent alpha-amylases, which suitably may be used for providing a hybrid with the desired mutations(s) according to the invention include the KSM-K36 and KSM-K38 alpha-amylases disclosed in EP 1,022,334 (hereby incorporated by reference).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

INDUSTRIAL APPLICATIONS

The alpha-amylase variants of this invention possess valuable properties allowing for a variety of industrial applications. In particular, enzyme variants of the invention are applicable as a component in washing, dishwashing, and hard surface cleaning detergent compositions.

Variant of the invention with altered properties may be used for starch processes, in particular starch conversion, especially liquefaction of starch (see, e.g., U.S. Pat. No. 3,912,590, EP patent publications Nos. 252730 and 63909, WO 99/19467, and WO 96/28567, which are all hereby incorporated by reference). Also contemplated are compositions for starch conversion purposes, which may beside the variant of the invention also comprise an AMG, pullulanase, and other alpha-amylases.

Further, variants of the invention are also particularly useful in the production of sweeteners and ethanol (see, e.g., U.S. Pat. No. 5,231,017 hereby incorporated by reference), such as fuel, drinking and industrial ethanol, from starch or whole grains.

A variant of the invention may also be used for textile desizing (see, e.g., WO 95/21247, U.S. Pat. No. 4,643,736, and EP 119,920, which are hereby incorporated by reference).

Detergent Compositions

As mentioned above, variants of the invention may suitably be incorporated in detergent compositions. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a protease, a lipase, a peroxidase, another amylolytic enzyme, glucoamylase, maltogenic amylase, CGTase and/or a cellulase, mannanase (such as Mannaway™ from Novozymes, Denmark)), pectinase, pectine lyase, cutinase, laccase, and/or another alpha-amylase.

Alpha-amylase variants of the invention may be incorporated in detergents at conventionally employed concentrations. It is at present contemplated that a variant of the invention may be incorporated in an amount corresponding to 0.00001-10 mg (calculated as pure, active enzyme protein) of alpha-amylase per liter of wash/dishwash liquor using conventional dosing levels of detergent.

Compositions

The invention also relates to a composition comprising a variant of the invention, and in a preferred embodiment also a *B. stearothermophilus* alpha-amylase (BSG), in particular a variant thereof.

In another embodiment the composition comprises beside a variant of the invention a glucoamylase, in particular a glucoamylase originating from *Aspergillus niger* (e.g., the G1 or G2 *A. niger* AMG disclosed in Boel et al., 1984, "Glucoamylases G1 and G2 from *Aspergillus niger* are synthesized from two different but closely related mRNAs", *EMBO J.* 3(5): 1097-1102, or a variant therefore, in particular a variant disclosed in WO 00/04136 or WO 01/04273 or the *Talaromyces emersonii* AMG disclosed in WO 99/28448.

A specific combination is LE399 and a variant disclosed in WO 00/04136 or WO 01/04273, in particular a variant with one or more of the following substitutions:

N9A, S56A, V59A, S119P, A246T, N313G, E342T, A393R, S394R, Y402F, E408R, in particular a variant with all mutation.

In an embodiment the composition of the invention also comprises a pullulanase, in particular a *Bacillus* pullulanase.

Materials and Methods

Enzymes:

*Bacillus licheniformis* alpha-amylase shown in SEQ ID NO: 8 and also available from Novozymes.

AA560: SEQ ID NO: 12; disclosed in WO 00/60060; deposited on 25 Jan. 1999 at DSMZ and assigned the DSMZ no. 12649. AA560 was deposited by the inventors under the terms of the Budapest Treaty on the International Recognition of the Deposit of Microorganisms for the Purposes of Patent Procedure at Deutshe Sammmlung von Microorganismen and Zellkulturen GmbH (DSMZ), Mascheroder Weg 1b, D-38124 Braunschweig DE.

LB medium (In 1 liter $H_2O$: 10 g bacto-tryptone, 5 g bacto-yeast extract, 10 g NaCl, pH adjusted to 7.0 w. NaOH, autoclaved).

TY agar plates (In 1 liter $H_2O$: 16 g bacto-tryptone, 10 g bacto-yeast extract, 5 g NaCl, pH adjusted to 7.0 w. NaOH, and 15 g bacto-agar is added prior to autoclaving).

10% Lugol solution (Iodine/Potassium iodine solution; made by 10-fold dil. in $H_2O$ of stock: Sigma Cat. no. L 6146).

*Bacillus subtilis* SHA273: see WO 95/10603

Plasmids pDN1528 contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9 of WO 96/23874.

Methods:

Low pH Filter Assay

*Bacillus* libraries are plated on a sandwich of cellulose acetate (OE 67, Schleicher & Schuell, Dassel, Germany)— and nitrocellulose filters (Protran-Ba 85, Schleicher & Schuell, Dassel, Germany) on TY agar plates with 10 micrograms/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants in the LE399 backbone). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

Secondary Screening

Positive transformants after rescreening are picked from the storage plate and tested in a secondary plate assay. Positive transformants are grown for 22 hours at 37° C. in 5 ml LB+chloramphenicol. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 microliter sample is spotted on an assay plate. The assay plate is stained with 10% Lugol solution. Improved variants are seen as variants with higher residual activity (detected as halos on the assay plate) than the backbone. The improved variants are determined by nucleotide sequencing.

Stability Assay of Unpurified Variants:

*Bacillus* cultures expressing the variants to be analyzed are grown for 21 hours at 37° C. in 10 ml LB+chloramphenicol. 800 microliter culture is mixed with 200 microliters citrate buffer, pH 4.5. A number of 70 microliter aliquots corresponding to the number of sample time points are made in PCR tubes and incubated at 70° C. (for variants in the wt backbone) or 90° C. (for variants in LE399) for various time points (typically 5, 10, 15, 20, 25 and 30 minutes) in a PCR machine. The 0 min sample is not incubated at high temperature. Activity in the sample is measured by transferring 20 microliters to 200 microliters of the alpha-amylase PNP-G7 substrate MPR3 ((Boehringer Mannheim Cat. no. 1660730) as described below under "Assays for Alpha-Amylase Activity". Results are plotted as percentage activity (relative to the 0 time point) versus time, or stated as percentage residual activity after incubation for a certain period of time.

Fermentation and Purification of Alpha-Amylase Variants

A *B. subtilis* strain harboring the relevant expression plasmid is streaked on an LB-agar plate with 10 micrograms/ml kanamycin from −80° C. stock, and grown overnight at 37° C.

The colonies are transferred to 100 ml PS-1 media supplemented with 10 micrograms/ml chloamphinicol in a 500 ml shaking flask.

| Composition of PS-1 medium: | |
|---|---|
| Pearl sugar | 100 g/l |
| Soy Bean Meal | 40 g/l |
| $Na_2HPO_4, 12H_2O$ | 10 g/l |
| PluronicTM PE 6100 | 0.1 g/l |
| $CaCO_3$ | 5 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2 M NaCl in the same buffer. The eluate is dialysed against 10 mM Tris, pH 9.0 and applied on a Q-sepharose F.F. and eluted with a linear gradient from 0-0.3 M NaCl over 6 column volumes. The fractions that contain the activity (measured by the Phadebas assay) are pooled, pH was adjusted to pH 7.5 and remaining color was removed by a treatment with 0.5% W/vol. active coal in 5 minutes.

Stability Determination of Purified Variants

All stability trials of purified variants are made using the same set up. The method is as follows:

The enzyme is incubated under the relevant conditions (1-4). Samples are taken at various time points, e.g., after 0, 5, 10, 15 and 30 minutes and diluted 25 times (same dilution for all taken samples) in assay buffer (0.1 M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Specific Activity Determination

The specific activity is determined using the Phadebas assay (Pharmacia) as activity/mg enzyme. The manufacturer's instructions are followed (see also below under "Assay for α-amylase activity").

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue color will be produced. The color intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G7 substrate. PNP-G7 which is a abbreviation for p-nitrophenyl-alpha,D-maltoheptaoside is a blocked oligosaccharide which can be cleaved by an endo-amylase. Following the cleavage, the alpha-glucosidase included in the kit digest the substrate to liberate a free PNP molecule which has a yellow colour and thus can be measured by visible spectophometry at λ=405 nm (400-420 nm). Kits containing PNP-G7 substrate and alpha-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 microliter sample to a 96 well microtiter plate and incubating at 25° C. 200 microliters reagent solution pre-equilibrated to 25° C. is added. The solution is mixed and pre-incubated 1 minute and absorption is measured every 30 sec. over 4 minutes at OD 405 nm in an ELISA reader.

The slope of the time dependent absorption-curve is directly proportional to the activity of the alpha-amylase in question under the given set of conditions.

EXAMPLES

Example 1

Construction, by error-prone PCR mutagenesis, of *Bacillus licheniformis* alpha-amylase variants having an improved stability at low pH, high temperature and low calcium ion concentration compared to the parent enzyme.

Error-Prone PCR Mutagenesis and Library Construction

To improve the stability at low pH and low calcium concentration of the parent *Bacillus licheniformis* alpha-amylase, error-prone PCR mutagenesis was performed. The plasmid pDN1528 encoding the wild-type *Bacillus licheniformis* alpha-amylase gene was utilized as template to amplify this gene with primers: 22149: 5'-CGA TTG CTG ACG CTG TTA TTT GCG-3' (SEQ ID NO: 14) and 24814: 5'-GAT CAC CCG CGA TAC CGT C-3' (SEQ ID NO: 15) under PCR conditions where increased error rates leads to introduction of random point mutations. The PCR conditions utilized were: 10 mM Tris-HCl, pH 8.3, 50 mM KCl, 4 mM MgCl$_2$, 0.3 mM MnCl$_2$, 0.1 mM dGTP/dATP, 0.5 mM dTTP/dCTP, and 2.5 units Taq polymerase per 100 microliter reaction.

The resultant PCR fragment was purified on gel and used in a PCR-based multimerization step with a gel purified vector fragment created by PCR amplification of pDN1528 with primers #24: 5'-GAA TGT ATG TCG GCC GGC AAA ACG CCG GTG A-3' (SEQ ID NO: 16) and #27: 5''-GCC GCC GCT GCT GCA GAA TGA GGC AGC AAG-3' (SEQ ID NO: 17) forming an overlap to the insert fragment. The multimerization reaction was subsequently introduced into *B. subtilis* (Shafikhani et al., 1997, *Biotechniques* 23: 304-310).

Screening

The error-prone library described above was screened in the low pH filter assay (see "Materials & Methods"). Clones testing positive upon rescreening was submitted to secondary screening for stability in the liquid assay described in Materials and Methods.

Results:

Increased Stability at pH 4.5, 5 ppm Calcium Incubated at 90° C.

| Name | wt | LE488 | LE489 | 7.19.1 | 8.9.1 |
|---|---|---|---|---|---|
| Mutations | — | D207V | K170Q<br>D207V<br>N280S | E132A<br>D207V | D207E<br>E250G<br>H406L<br>L427I |
| Stability1) | — | + | + | + | + |

1)A "+" indicates significant increase in stability relative to wild type.

Increased Stability at pH 4.5, 5 ppm Calcium Incubated at 90° C.

| Name | wt | LE491 | LE492 | LE493 | LE494 | 19.3.1 |
|---|---|---|---|---|---|---|
| Mutations | — | D60N<br>D207V<br>L318M | T49I<br>E132V<br>V440A | T49I<br>K176R<br>D207V<br>Y402F | Q374R<br>E385V<br>Q393R | N190F<br>A209V<br>Q264S |
| Stability1) | — | + | + | + | + | + |

1)A "+" indicates significant increase in stability relative to wt.

Increased Stability at pH 4.5, 5 ppm Calcium Incubated at 90° C.

| Name | wt | E132-1 | D207-7 | D207-6 | E250-8 |
|---|---|---|---|---|---|
| Mutations | — | E132P | D207L | D207G | E250F |
| Stability1) | — | + | + | + | + |

1)A "+" indicates significant increase in stability relative to wt.

Example 2

Transfer, by site-directed mutagenesis, of a selection of mutations from Example 1 to a new (non-wild type) backbone to improve stability at low pH and low calcium ion concentration compared to the parent enzyme.

Site-Directed Mutagenesis

Mutations from LE493 (K176R+D207V+Y402F) were transferred to LE399 yielding LE495. This was performed by the overlap PCR method (Kirchhoff and Desrosiers, 1993, PCR Methods and Applications, 2: 301-304). 2 overlapping PCR fragments were generated by amplification of the LE399 template with the primers: Fragment A: #312 Mut176 5'-CCC GAA AGC TGA ACC GCA TCT ATA GGT TTC AAG GGA AGA CTT GGG ATT-3' (SEQ ID NO: 18) (mutated codon indicated in bold) and #290 D207overlap 5'-AGG ATG GTC ATA ATC AAA GTC GG-3'(SEQ ID NO: 19); Fragment B: #313 Mut207 5'-CCG ACT TTG ATT ATG ACC ATC CTG TTG TCG TAG CAG AGA TTA AGA GAT GGG G-3' (SEQ ID NO: 20) and #314 Mut402 5'-CGA CAA TGT CAT GGT GGT CGA AAA AAT CAT GCT GTG CTC CGT ACG-3' (SEQ ID NO: 21). Fragments A and B were mixed in equimolar ratios and subsequently the full-length fragment was amplified with the external primers: #312 Mut176 and #314 Mut402. This fragment was used in a multimerization reaction with the vector PCR fragment created with the primers #296 Y402multi 5'-TTT CGA CCA CCA TGA CAT TGT CG-3' (SEQ ID NO: 22) and #305 399Multi176 5'-TAT AGA TGC GGT TCA GCT TTC GGG-3' (SEQ ID NO: 23) on template LE399 as described above. The multimerization reaction was subsequently transformed into *B. subtilis*. Clones were screened for stability in the assay mentioned above. The presence of the mutations from LE493 in several clones with increased stability was confirmed by sequencing.

LE 497 was obtained in a similar manner by amplifying the LE399 encoding template with primers #312 Mut176 and #314 Mut402 and using the resulting PCR fragment in a multimerization reaction with a vector fragment obtained by PCR amplification of the LE399 template with the primers #296 Y402multi and #305 399Multi176.

Results:

Stabilization of LE399 Variant at pH 4.5, 5 ppm Calcium Incubated at 90° C.

| | Name | | |
|---|---|---|---|
| | LE399 | LE495 | LE497 |
| Mutations | —<br>(backbone) | K176R<br>D207V<br>Y402F | K176R<br>Y402F |
| Stability1) | — | + | + |

1)A "+" indicates significant increase in stability relative to backbone.

The invention claimed is:

1. An isolated variant of a parent alpha-amylase, wherein:
   (a) the variant has at least 90% sequence identity to SEQ ID NO: 6,
   (b) the variant comprises a substitution of serine at position 239 relative to the parent alpha-amylase, using the amino acid sequence of SEQ ID NO: 8 for determining position numbering, and
   (c) the variant has increased thermostability relative to the parent alpha-amylase, wherein thermostability is determined at pH 4.5, 90° C. and 5 ppm calcium and has alpha-amylase activity.

2. The variant of claim 1, wherein the variant has at least 95% sequence identity to SEQ ID NO: 6.

3. The variant of claim 1, wherein the variant has at least 97% sequence identity to SEQ ID NO: 6.

4. The variant of claim 1, wherein the variant has at least 99% sequence identity to SEQ ID NO: 6.

5. The variant of claim 1, wherein the parent alpha-amylase is a Bacillus stearothermophilus alpha-amylase.

6. The variant of claim 5, wherein the Bacillus stearothermophilus alpha-amylase is the amino acid sequence of SEQ ID NO: 6.

7. The variant of claim 1, wherein the variant further comprises an alteration at one or more positions selected from the group consisting of 49, 60, 104, 132, 161, 170, 176, 179, 180, 181, 183, 200, 203, 204, 207, 212, 237, 250, 280, 298, 318, 374, 385, 393, 402, 406, 427, 430, 440, 444, 447, and 482, wherein the alteration(s) are independently selected from an insertion, a deletion, or a substitution.

8. A composition comprising the variant of claim 1 and (i) another alpha-amylase; or (ii) one or more enzymes selected from the group consisting of glucoamylase, phytase, and pullalanase.

9. An isolated variant of a parent alpha-amylase, wherein:
   (a) the variant has an amino acid sequence with 1-15 alteration(s) relative to the parent alpha-amylase, wherein
      (i) the 1-15 alteration(s) are independently selected from an insertion, a deletion, or a substitution, and
      (ii) the 1-15 alteration(s) include a substitution of serine at position 239, and
   (b) the parent alpha-amylase has at least 90% sequence identity to SEQ ID NO: 6, and
   (c) the amino acid sequence of SEQ ID NO: 8 is used for determining position numbering; and
   (d) the variant has increased thermostability relative to the parent alpha-amylase, wherein thermostability is determined at pH 4.5, 90° C. and 5 ppm calcium and has alpha-amylase activity.

10. The variant of claim 9, wherein the alteration(s) are substitution(s).

11. The variant of claim 9, wherein the variant has 1 alteration relative to the parent alpha-amylase which is the substitution of the amino acid at position 239.

12. The variant of claim 9, wherein the parent alpha-amylase has at least 95% sequence identity to SEQ ID NO: 6.

13. The variant of claim 9, wherein the parent alpha-amylase has at least 99% sequence identity to SEQ ID NO: 6.

14. The variant of claim 9, wherein one or more alteration(s) are at a position selected from the group consisting of 49, 60, 104, 132, 161, 170, 176, 179, 180, 181, 183, 200, 203, 204, 207, 212, 237, 250, 280, 298, 318, 374, 385, 393, 402, 406, 427, 430, 440, 444, 447, and 482.

15. A composition comprising the variant of claim 9 and (i) another alpha-amylase or (i) one or more enzymes selected from the group consisting of glucoamylase, phytase.

16. An isolated variant of a *Bacillus stearothermophilus* alpha-amylase, wherein the variant consists of a substitution of serine at position 239 with a different amino acid, using the amino acid sequence of SEQ ID NO: 8 for determining position numbering, wherein the variant has increased thermostability relative to the parent alpha-amylase, wherein thermostability is determined at pH 4.5, 90° C. and 5 ppm calcium and has alpha-amylase activity.

17. The variant of claim 16, wherein the *Bacillus stearothermophilus* alpha-amylase is the amino acid sequence of SEQ ID NO: 6.

* * * * *

UNITED STATES PATENT AND TRADEMARK OFFICE
CERTIFICATE OF CORRECTION

| | |
|---|---|
| PATENT NO. | : 7,713,723 B1 |
| APPLICATION NO. | : 12/645116 |
| DATED | : May 11, 2010 |
| INVENTOR(S) | : Thisted et al. |

It is certified that error appears in the above-identified patent and that said Letters Patent is hereby corrected as shown below:

Title page 2, in the list of Foreign Patent Documents, delete

"WO 99/09183     2/2000" and insert

-- WO 99/09183     2/1999 --.

Signed and Sealed this

Fifteenth Day of June, 2010

David J. Kappos
*Director of the United States Patent and Trademark Office*